United States Patent
Piron et al.

(10) Patent No.: US 11,207,139 B2
(45) Date of Patent: Dec. 28, 2021

(54) 3D NAVIGATION SYSTEM AND METHODS

(71) Applicant: SYNAPTIVE MEDICAL INC., Toronto (CA)

(72) Inventors: Cameron Anthony Piron, Toronto (CA); Michael Frank Gunter Wood, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 175 days.

(21) Appl. No.: 16/346,498

(22) PCT Filed: Oct. 31, 2016

(86) PCT No.: PCT/CA2016/051264
§ 371 (c)(1),
(2) Date: Apr. 30, 2019

(87) PCT Pub. No.: WO2018/076094
PCT Pub. Date: May 3, 2018

(65) Prior Publication Data
US 2019/0254757 A1    Aug. 22, 2019

(51) Int. Cl.
*A61B 5/00* (2006.01)
*A61B 34/20* (2016.01)
(Continued)

(52) U.S. Cl.
CPC .............. *A61B 34/20* (2016.02); *A61B 5/742* (2013.01); *A61B 5/7405* (2013.01);
(Continued)

(58) Field of Classification Search
CPC ......... A61B 34/20; A61B 34/76; A61B 90/20; G02B 21/0012
See application file for complete search history.

(56) References Cited

U.S. PATENT DOCUMENTS

2004/0106916 A1* 6/2004 Quaid ................... A61B 34/76
606/1
2008/0010706 A1   1/2008 Moses et al.
(Continued)

FOREIGN PATENT DOCUMENTS

| CA | 2892554 A1 | 9/2014 |
| CA | 2929702 A1 | 9/2014 |
| WO | 2006095027 A1 | 9/2006 |

OTHER PUBLICATIONS

International Search Report and Written Opinion issued by the International Searching Authority in relation to corresponding PCT application No. PCT/CA2016/051264 dated Jul. 25, 2017; 14 pgs.
(Continued)

*Primary Examiner* — Joel F Brutus

(57) ABSTRACT

A 3D navigation system and methods for enhancing feedback during a medical procedure, involving: an optical imaging system having an optical assembly comprising movable zoom optics and movable focus optics, a zoom actuator for positioning the zoom optics, a focus actuator for positioning the focus optics, a controller for controlling the zoom actuator and the focus actuator in response to received control input, at least one detector for capturing an image of at least one of a target and an obstacle, the at least one detector operable with the optical assembly, and a proprioception feature operable with the optical imaging system for generating a 3D perception, the proprioception feature comprising a communication feature for providing 3D information, the 3D information comprising real-time depth information in relation to real-time planar information within an interrogation volume.

20 Claims, 17 Drawing Sheets

(51) Int. Cl.
    *A61B 90/20*     (2016.01)
    *A61B 90/00*     (2016.01)
    *A61B 8/08*     (2006.01)
    *G02B 21/00*     (2006.01)
    *G02B 21/22*     (2006.01)
    *G02B 21/36*     (2006.01)
    *G06F 3/16*     (2006.01)
    *A61B 90/30*     (2016.01)
    *A61B 34/30*     (2016.01)
    *A61B 34/00*     (2016.01)
    *A61B 34/10*     (2016.01)
    *A61B 17/34*     (2006.01)
    *A61B 17/00*     (2006.01)
    *A61B 90/50*     (2016.01)

(52) U.S. Cl.
    CPC .......... *A61B 5/7455* (2013.01); *A61B 8/0841* (2013.01); *A61B 34/00* (2016.02); *A61B 34/30* (2016.02); *A61B 34/76* (2016.02); *A61B 90/20* (2016.02); *A61B 90/30* (2016.02); *A61B 90/361* (2016.02); *A61B 90/37* (2016.02); *G02B 21/0012* (2013.01); *G02B 21/22* (2013.01); *G02B 21/36* (2013.01); *G06F 3/167* (2013.01); *A61B 17/3421* (2013.01); *A61B 2017/00973* (2013.01); *A61B 2034/107* (2016.02); *A61B 2034/2051* (2016.02); *A61B 2034/2055* (2016.02); *A61B 2034/2057* (2016.02); *A61B 2034/2063* (2016.02); *A61B 2034/2065* (2016.02); *A61B 2034/2068* (2016.02); *A61B 2034/2074* (2016.02); *A61B 2090/309* (2016.02); *A61B 2090/363* (2016.02); *A61B 2090/3614* (2016.02); *A61B 2090/371* (2016.02); *A61B 2090/378* (2016.02); *A61B 2090/508* (2016.02)

(56) References Cited

U.S. PATENT DOCUMENTS

| | | |
|---|---|---|
| 2008/0303899 A1* | 12/2008 | Berci ................. A61B 1/00188 348/74 |
| 2011/0019884 A1 | 1/2011 | Blau |
| 2014/0107471 A1* | 4/2014 | Haider ............... A61B 17/1703 600/424 |
| 2015/0272694 A1 | 10/2015 | Charles |
| 2016/0030131 A1 | 2/2016 | Yang et al. |
| 2016/0242855 A1 | 8/2016 | Fichtinger et al. |
| 2016/0242858 A1 | 8/2016 | Moctezuma De La Barrera et al. |

OTHER PUBLICATIONS

Search report issued by the Intellectual Property Office of the UK in relation to GB Application No. GB1907704.9 dated Aug. 24, 2021, 7 pgs.

* cited by examiner

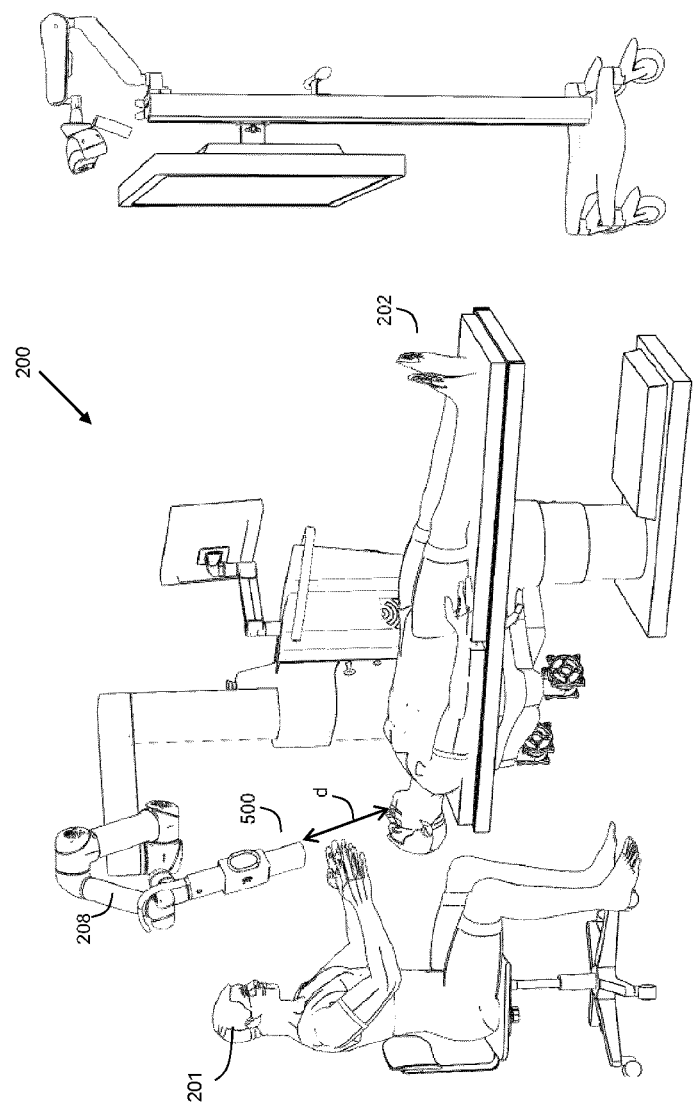

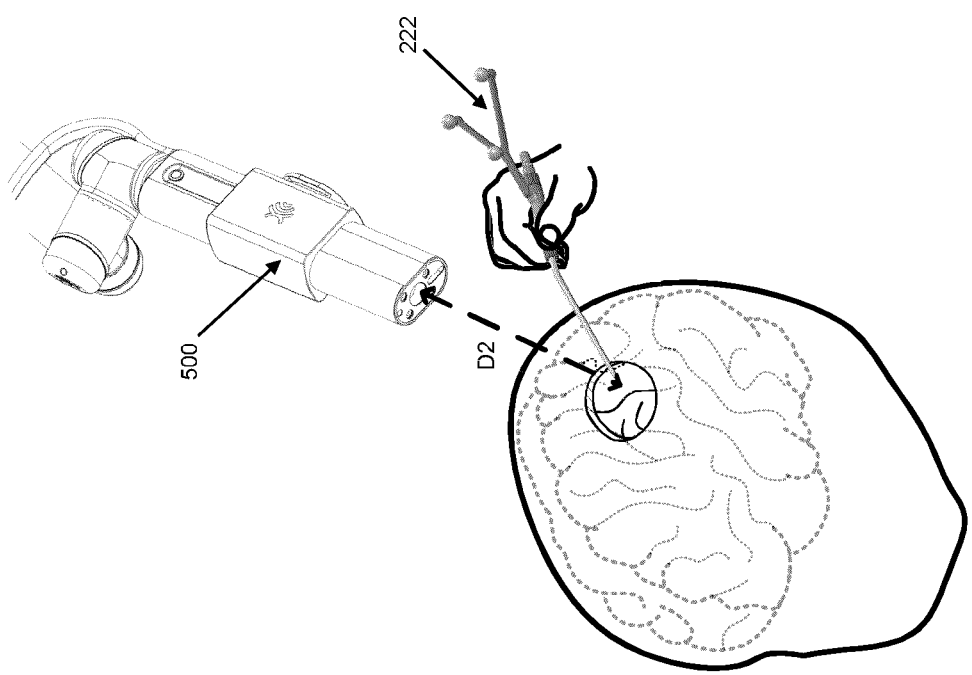
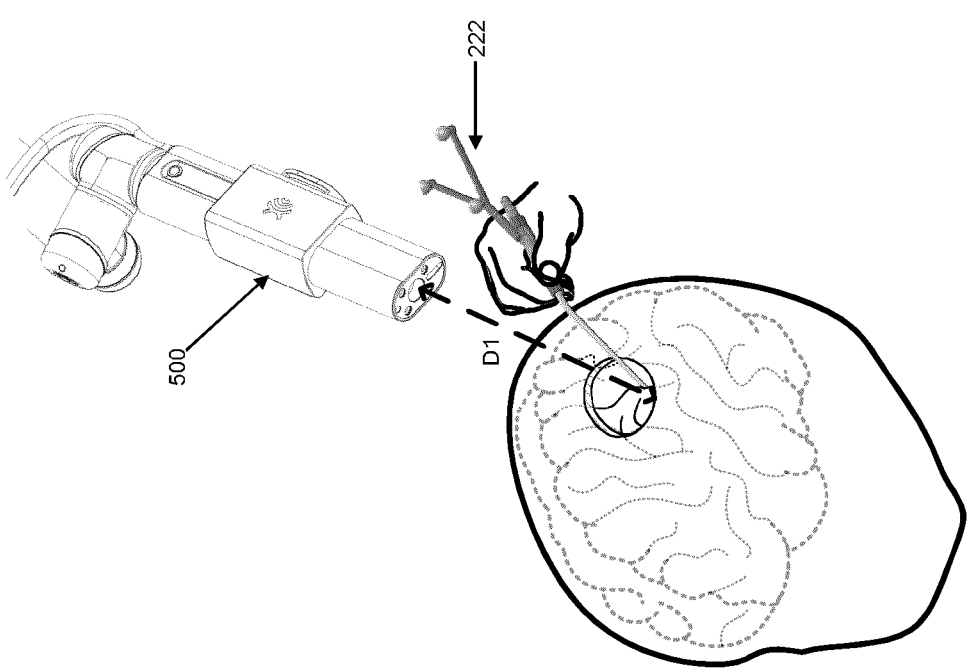
FIG. 11

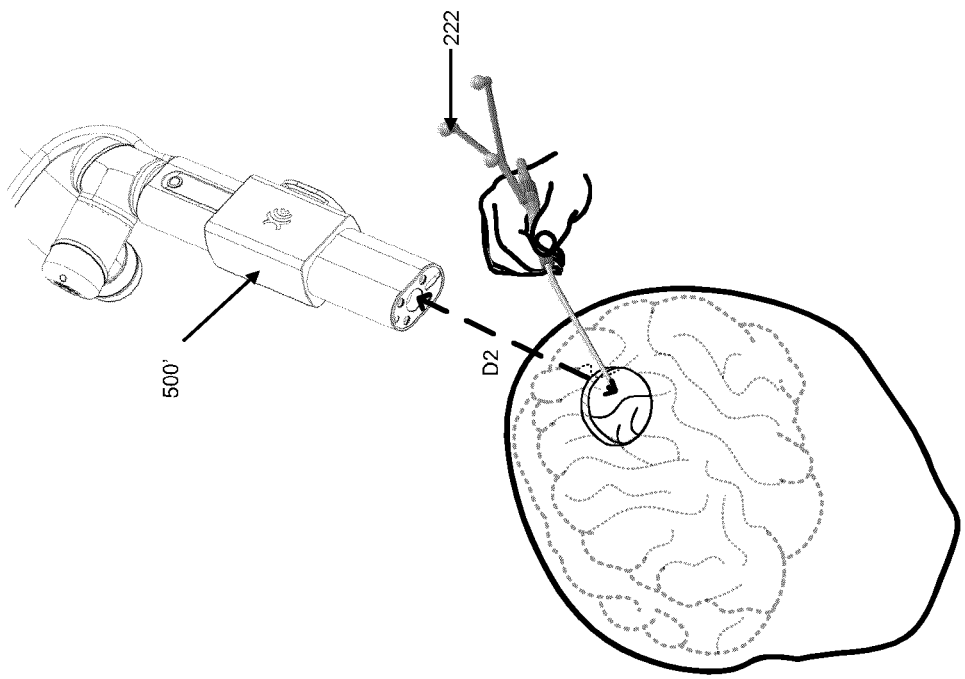
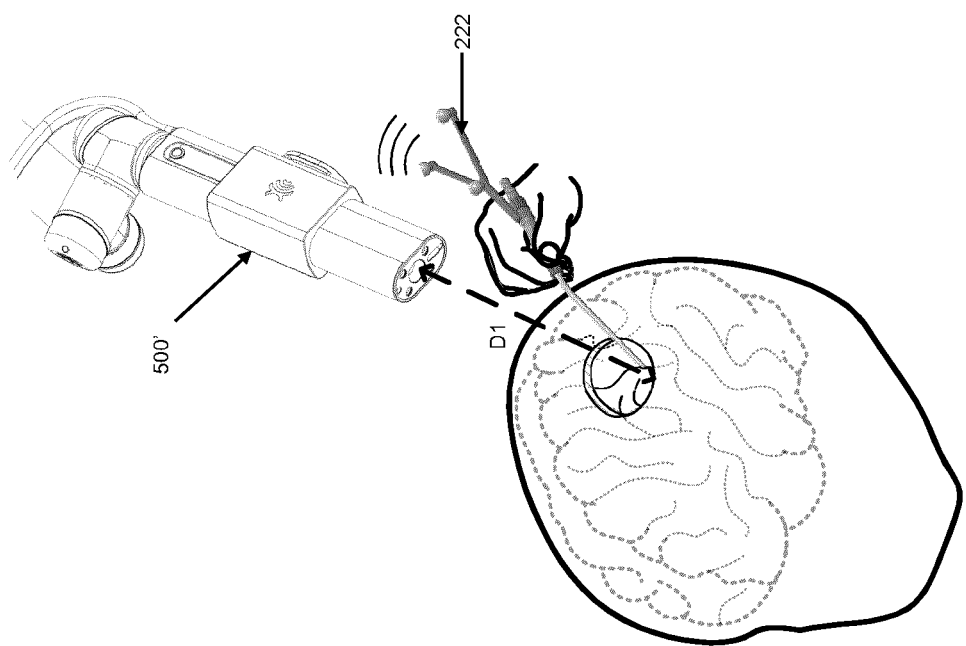
FIG. 13

3D NAVIGATION SYSTEM AND METHODS

CROSS-REFERENCE TO RELATED APPLICATION(S)

This document is a national stage entry application claiming the benefit of, and priority to, International Patent Application No. PCT/CA2016/051264, filed Oct. 31, 2016, entitled "3D NAVIGATION SYSTEM AND METHODS," hereby incorporated by reference in its entirety.

TECHNICAL FIELD

Generally, the present disclosure technically relates to optical imaging systems. More particularly, the present disclosure technically relates to optical imaging systems for use in image guided medical procedures. Even more particularly, the present disclosure technically relates to optical imaging systems for use in image guided medical procedures involving a pointer tool.

BACKGROUND

In the related art, conventional surgical microscopes are often used during surgical procedures to provide a detailed or magnified view of the surgical site. In some cases, separate narrow field and wide field scopes are used within the same surgical procedure to obtain image views with different zoom ranges. Often, adjusting the zoom and focus of such a related art surgical microscope requires the user, e.g., a surgeon, to manually adjust the optics of the microscope, which is difficult, time-consuming, and frustrating, particularly during a surgical procedure.

Further, related art image capture cameras and light sources are components that are separate from the related art surgical microscope. Typically, the specific camera and light source used with a given conventional surgical microscope are different for different medical centers and even for different surgical procedures within the same medical center. This circumstance results in an inconsistency in the images obtained, wherein comparing images between different medical centers is difficult or impossible.

In related art surgical navigation, differences between conventional stereoscopic optical chains and video telescopic microscopy optical chains exist, e.g., mechanisms used for generating 3-dimensional (3D) perception at high magnification. However, such differences usually require substantial human correction in an attempt to gauge a target location in the depth dimension. Over the previous decade, many related art surgical systems do not include any 3D perception features for at least that 3D perception has been believed to be a barrier to endoscopic surgery, e.g., endonasal surgery, in the related art.

In addition, various related art navigation devices are used, such as a white probing stick for visually-challenged persons, such as a white probing stick that receives feedback in the form of a sound via echo location, two ultrasonic stereoscopic scanners for translating into an audio tone, and a motor vehicle backup camera system, wherein an audible sound or an indicator light is produced for collision warning. However, these related art devices do not address challenges in the area of surgical navigation.

As such, the related art navigation systems have experienced many challenges, including difficulty in accurately providing a surgeon with sufficient feedback relating to target depth in performing navigated surgery using only stereo imaging and surgeon eye strain. Therefore, a need exists for a navigation system that improves both planar and depth perception in relation to a surgical interrogation volume to overcome many of the related art challenges.

SUMMARY

In addressing at least many of the challenges experienced in the related art, the subject matter of the present disclosure involves systems and methods which consider 3D perception being an operator's ability to generate the relative positional sense (RPS) of objects located within a given interrogation volume. Multiple mechanisms exist for generating 3D perception, wherein binocular vision is an important and powerful tactic. The perception of the relative position of two objects is also achieved and enhanced through the use of proprioception, shadowing, sound, as well as other factors, whereby all such factors synergistically interact, in accordance with embodiment of the present disclosure. The 3D navigation systems and methods of the present disclosure involve features for acquiring data from vision, touch, sound, e.g., via a tracked tool; translating the data into a usable form for a surgeon; and presenting information, based on the translated data, to the surgeon, wherein the information comprises 3D information is related to at least two of three senses, e.g., vision, touch, and sound, capture, wherein the information is applicable to a particular context of use, e.g., a surgical context.

In some examples, the present disclosure provides an optical imaging system for imaging a target during a medical procedure. The system includes: an optical assembly including movable zoom optics and movable focus optics; a zoom actuator for positioning the zoom optics; a focus actuator for positioning the focus optics; a controller for controlling the zoom actuator and the focus actuator in response to received control input; and a camera for capturing an image of the target from the optical assembly, wherein the zoom optics and the focus optics are independently movable by the controller using the zoom actuator and the focus actuator, respectively, and wherein the optical imaging system is configured to operate at a minimum working distance (WD) from the target, the WD being defined between an aperture of the optical assembly and the target.

In some examples, the present disclosure provides a processor for controlling the optical imaging system disclosed herein. The processor is configured to: provide a user interface to receive control input, via an input device coupled to the processor, for controlling the zoom actuator and the focus actuator; transmit control instructions to the controller of the optical imaging system to adjust zoom and focus in accordance with the control input; and receive image data from the camera for outputting to an output device coupled to the processor.

In some examples, the present disclosure provides a system for optical imaging during a medical procedure. The system comprises: the optical imaging system disclosed herein; a positioning system for positioning the optical imaging system; and a navigation system for tracking each of the optical imaging system and the positioning system relative to the target.

In some examples, the present disclosure provides a method of autofocusing using an optical imaging system during a medical procedure, the optical imaging system comprising motorized focus optics and a controller for positioning the focus optics. The method includes: determining a WD between an imaging target and an aperture of the optical imaging system; determining a desired position of the focus optics based on the WD; and positioning the focus optics at the desired position.

In accordance with an embodiment of the present disclosure, a 3D navigation system for enhancing feedback during a medical procedure comprises: an optical imaging system comprising: an optical assembly comprising movable zoom optics and movable focus optics; a zoom actuator for positioning the zoom optics; a focus actuator for positioning the focus optics; a controller for controlling the zoom actuator and the focus actuator in response to received control input; at least one detector for capturing an image of at least one of a target and an obstacle, the at least one detector operable with the optical assembly; and a proprioception feature operable with the optical imaging system for generating a 3D perception, the proprioception feature comprising a communication feature for providing 3D information, the 3D information comprising real-time depth information in relation to real-time planar information in relation to an interrogation volume, the zoom optics and the focus optics independently movable by the controller by way of the zoom actuator and the focus actuator, respectively, and the optical imaging system configured to operate at a minimum WD from at least one of the target and the obstacle, the WD defined between an aperture of the optical assembly and at least one of the target and the obstacle, whereby feedback during the medical procedure is enhanceable. The obstacle may be an anatomical structure or any other structure, such as a surgical tool, a synthetic anatomical structure, an implanted structure, a transplanted structure, a grafted structure, and the like, by example only.

In accordance with an embodiment of the present disclosure, a method of fabricating a 3D navigation system for enhancing feedback during a medical procedure comprises: providing an optical imaging system, providing the optical imaging system comprising: providing an optical assembly comprising providing movable zoom optics and providing movable focus optics; providing a zoom actuator for positioning the zoom optics; providing a focus actuator for positioning the focus optics; providing a controller for controlling the zoom actuator and the focus actuator in response to received control input; providing at least one detector for capturing an image of at least one of a target and an obstacle, providing the at least one detector comprising providing the at least one detector as operable with the optical assembly; and providing a proprioception feature operable with the optical imaging system for generating a 3D perception, providing the proprioception feature comprising providing a communication feature configured to provide 3D information, the 3D information comprising real-time depth information in relation to real-time planar information in relation to an interrogation volume, providing the zoom optics and providing the focus optics comprising providing the zoom optics and providing the focus optics as independently movable by the controller by way of the zoom actuator and the focus actuator, respectively, and providing the optical imaging system comprising configuring the optical imaging system to operate at a minimum WD from at least one of the target and the obstacle, the WD defined between an aperture of the optical assembly and at least one of the target and the obstacle, whereby feedback during the medical procedure is enhanceable.

In accordance with an embodiment of the present disclosure, a method enhancing feedback during a medical procedure by way of a 3D navigation system comprises: providing the 3D navigation system, providing the 3D navigation system comprising: providing an optical imaging system, providing the optical imaging system comprising: providing an optical assembly comprising providing movable zoom optics and providing movable focus optics; providing a zoom actuator for positioning the zoom optics; providing a focus actuator for positioning the focus optics; providing a controller for controlling the zoom actuator and the focus actuator in response to received control input;

providing at least one detector for capturing an image of at least one of a target and an obstacle, providing the at least one detector comprising providing the at least one detector as operable with the optical assembly; and providing a proprioception feature operable with the optical imaging system for generating a 3D perception, providing the proprioception feature comprising providing a communication feature for providing 3D information, the 3D information comprising real-time depth information in relation to real-time planar information in relation to an interrogation volume, providing the zoom optics and providing the focus optics comprising providing the zoom optics and providing the focus optics as independently movable by the controller by way of the zoom actuator and the focus actuator, respectively, and providing the optical imaging system comprising configuring the optical imaging system to operate at a minimum WD from at least one of the target and the obstacle, the WD defined between an aperture of the optical assembly and at least one of the target and the obstacle, wherein providing the communication feature comprises providing at least one sensory input device and providing at least one sensory output device, and wherein providing the communication feature comprises providing the communication feature as operable by way of a set of executable instructions storable on a nontransitory memory device; receiving at least one input signal by the at least one sensory input device; and providing at least one output signal by the at least one sensory output device, thereby enhancing feedback during the medical procedure.

Some of the features in the present disclosure are broadly outlined in order that the section entitled Detailed Description is better understood and that the present contribution to the art by the present disclosure is better appreciated. Additional features of the present disclosure are described hereinafter. In this respect, understood is that the present disclosure is not limited in its application to the details of the components or steps set forth herein or as illustrated in the several figures of the drawing, but are capable of being carried out in various ways which are also encompassed by the present disclosure. Also, understood is that the phraseology and terminology employed herein are for illustrative purposes in the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

FIG. 5 is a diagram illustrating a perspective view of an example optical imaging system being used during a medical procedure, in accordance with an embodiment of the present disclosure.

FIG. 11 is a set of diagrams illustrating perspective views of an optical imaging system using a method of autofocusing relative to a medical instrument, in accordance with an embodiment of the present disclosure.

FIG. 13 is a set of diagrams illustrating perspective views of an optical imaging system, using a 3D navigation system, in accordance with an alternative embodiment of the present disclosure.

Figure 1:
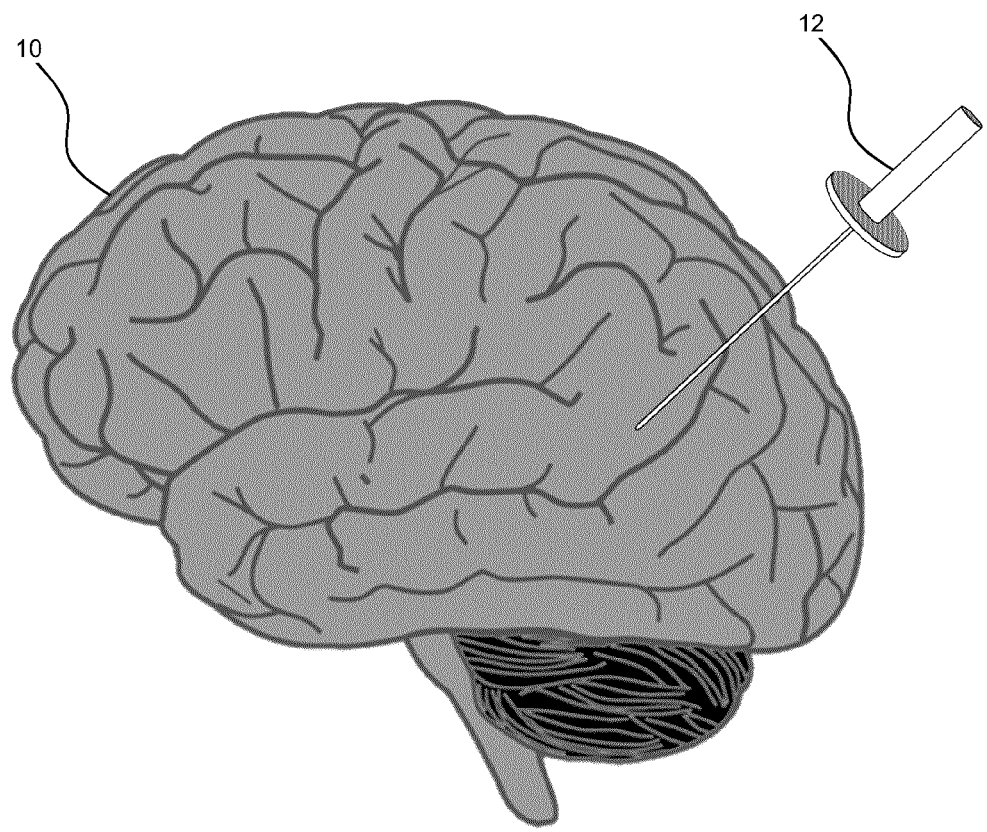
FIG. 1 is a diagram illustrating a perspective view of an access port inserted into a human brain, for providing access to internal brain tissue during an example medical procedure, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

The systems and methods described herein are useful in the field of neurosurgery, including oncological care, neurodegenerative disease, stroke, brain trauma, and orthopedic surgery. The subject matter of the present disclosure is applicable to other conditions or fields of medicine. Noted is that, while the present disclosure describes examples in the context of neurosurgery, the subject matter of the present disclosure is applicable to other surgical procedures that may use intraoperative optical imaging.

Various example apparatuses or processes are below-described. No below-described example embodiment limits any claimed embodiment; and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. The claimed embodiments optionally comprise any of the below-described apparatuses or processes.

Furthermore, numerous specific details are set forth in order to provide a thorough understanding of the disclosure. However, understood is that the embodiments described herein are practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" is understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures, e.g. minimally invasive medical procedures, are performed based on access to internal tissue through the access port.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest without having to spend excessive amounts of time and concentration repositioning tools, scopes and/or cameras during the medical procedure.

In accordance with embodiments of the present disclosure, the systems and methods consider the impact of the differences in generating feedback with 3D perception using binocular vision in relation to using proprioception. In particular, embodiments of the present discloser consider that vision facilitates locating peripheral targets more precisely and that proprioception facilitates greater precision for locating targets in the depth dimension. More particularly, the systems and methods of the present disclosure involve features which take into account that vision and proprioception have differential effects on the precision of target representation. When vision contributes to the target representation, localization is more precise along the lateral dimension, e.g., for locating the peripheral targets. However, when proprioception contributes to the target representation, localization is more precise in depth, e.g., locating deep targets in the tissue.

In particular, embodiments of the present disclosure consider several techniques for optimizing 3-D perception and, specifically, relative positional sense, at a high magnification. Such techniques include, but are not limited to, (a) implementing focused visual targets, e.g., maintaining the focal plane/point in conjunction with using visual obscuration throughout an interrogation volume and using a focused target in the depth dimension; (b) implementing serial focus adjustments, e.g., performing dynamic adjustment of the focal distance to create multiple focal points across a range of an interrogation volume; and (c) implementing an immersive contextual volume of view, e.g., generating a volume of view (VoV), wherein all of an anatomy is in simultaneous focus, thereby providing continuous contextual information throughout an interrogation volume.

In accordance with some embodiments of the present disclosure, the technique (a) is implementable with a conventional stereoscopic binocular microscope (CS-m), wherein large portions of the interrogation volume are obscured, and wherein a given target is maintained in constant focus. In implementing technique (a), embodiments of the present disclosure provide a very powerful mechanism to create 3D perception. For example, an operator's hands may come in and out of focus as the hands travel through a given VoV and approach a resolvable visual target within a volume of distortion, such as a basilar artery, thereby providing critical contextual information to the operator regarding focus, and whereby imperative visual cues of shadowing and distortion generate a framework for 3D perception and relative positional sense for facilitating navigation within the given VoV. In such embodiments, dynamic movement within a surgical cavity provides visual cues for generating a depth of field (DoF) at high magnification approximating that of an endoscope, wherein distortions are tolerated for a trade-off in 3D perception and magnification.

In accordance with some embodiments of the present disclosure, the technique (b) is implementable when distortions are deemed intolerable or the given visual target has changed. In implementing technique (b), an experienced operator (user) may be more tolerant of obscuration and less frequently adjusts the focal distance in relation to a less-experienced operator. Technique (b) is implementable for obtaining useful information in the DoF using a CS-m, but may require manual dynamic movements approximating that of an endoscope. An endoscope requires mechanical movement of the payload along the z-axis within a surgical cavity to redefine the plane of focus. Whereas a CS-m involves manually moving the focal distance and adjusting the focal point outside a surgical cavity, whereby greater flexibility is provided.

In accordance with some embodiments of the present disclosure, the technique (c) is implementable at high magnification in relation to a larger portion of a viewable anatomy, wherein imaging is simultaneously in focus and usable. If using a CS-m, at high magnification, imaging is serially adjusted to maintain focus of either a suprachiasmatic cistern or an interpeduncular cistern. If using a robotically operated video optical telescopic microscope (ROVOT-m), images are seen at the same optical parameters without manipulation.

In relation to technique (c), the visual cues of shadowing and distortion, otherwise provided by a CS-m as the operator's hands move past a blurred arterial structure (in a focal plane), optic nerve, and chiasm prior to arriving at a resolved basilar artery, are not provided if using a ROVOT-m. Thus, distortion is no longer available to generate a relative positional sense (RPS). However, the simultaneous contextual information of incrementally and clearly visualizing contents of cisterns provided to the operator is adequate compensation for creating a 3D perception and is useful for depth perception. In using a ROVOT-m, the RPS, while moving through the VoV, is generated by combining monitoring an operator's hands and receiving inherent haptic feedback, e.g., as the operator's hands move past the focal planes of the arterial structure, through the opticocarotid cistern, and arriving at the basilar artery, all of which have simultaneously been in focus. In using the 3D navigation system 1200 of the present disclosure, any inherent haptic feedback is enhanced with additional haptic feedback.

In accordance with some embodiments of the present disclosure, operator experience includes contextual knowledge of the anatomy and the relative location of the structures for facilitating perceiving an RPS of two structures. In using the systems and methods of the present disclosure, operator knowledge enhances the 3-D perception, especially during a learning curve thereof, i.e., the eye tends to be blind to what the mind does not know. A key component of systems and methods using the ROVOT-m further involves a global positioning system (GPS) for facilitating hands-free positioning of the payload, thereby further facilitating generating an RPS.

In accordance with some embodiments of the present disclosure, in compensating for an absence of contextual knowledge, the systems and methods use a second navigation screen with a tracked instrument displaying the relative position for a novice operator, thereby rapidly resolving any initial loss of depth perception, and thereby facilitating learning the relative position(s) of the anatomy within an interrogated volume by the novice operator. While simultaneous navigation is not absolutely required, the systems and methods use simultaneous navigation for added value by, not only shortening the learning curve, but also providing meaningful contextual information, e.g., by using dynamic continuous navigation via one display with simultaneous optical imaging on another display.

In accordance with some embodiments of the present disclosure, the systems and methods use two different visual input screens which in the aggregate synergistically created an immersive surgical volume, wherein all portions of the anatomy is resolvable and continuously referenced relative to one another, thereby minimizing a need for manual adjustment, and thereby providing enhanced "stereoscopy." The loss of distortion and shadowing as critical 3D visual navigation cues otherwise provided by a CS-m are easily compensated by the foregoing mechanisms in embodiments of the systems and methods that use the ROVOT-m. In addition, the systems and methods using the ROVOT-m facilitate working in an immersive surgical volume than a surgical volume in which anatomical portions are obscured for both experienced and novice operators.

In accordance with some embodiments of the present disclosure, the systems and methods use an untethered optical chain (OC), wherein a working axis of each operator hand is in a plane different than that of a viewing axis, whereby ergonomic value is enhanced, and whereby 3D perception is enhanced. With the CS-m they did not have the ability to look directly at their hands which were obscured by the intervening OC. In contrast, with the video telescopic microscopy (VT-m) systems, an operator may simply look down at the operator's hands approach the target and then look up at the monitor whenever magnification is desired. This manual technique (looking up and down) is another technique for adjusting, or compensating, loss of stereoscopy to generate 3D. While the operators are unaccustomed to having the liberty to directly see their hands and the wound, this technique is a source of 3D perception. However, when combined with the proprioception, these techniques are synergistically useful, particularly in applications associated with bimanual dissection, and are encompassed by embodiment so the present disclosure.

In accordance with some embodiments of the present disclosure, the systems and methods overcome related art challenges by involving at least proprioception features, whereby enhanced tactile and haptic feedback between the surgeons two hands and relative anatomy are provided, and whereby RPS and pother spatial sensing is generates. Complex procedures, such as clip ligation of aneurysms, carotid and pituitary transpositions, and dissection of brainstem perforators are increasingly performed by endonasal endoscopy. The systems and methods of the present disclosure involving 3D perception, e.g., via proprioception, enhance, not only endonasal endoscopy, but also enhance video-based telescopic neurosurgery and neurosurgical training programs.

In accordance with some embodiments of the present disclosure, the systems and methods involve various techniques for acquiring 3D data, e.g., using five senses to determine location(s), such as inward and outward precession in a spiral pattern within an interrogation volume. For generating (translating) the 3D data into 3D information, a plurality of input data types are used, such as a combination of sound and haptic/proprioception data, a combination of visual and haptic/proprioception data, and a combination of a cross-sectional view of a brain and a view of the brain, wherein selected combinations are displayable in relation to a same field of view (FoV). Audio feedback for indicating a trajectory to target eliminates full reliance on merely visible feedback, e.g., audio feedback for a cannulation procedure.

Referring to FIG. 1, this diagram illustrates, in a perspective view, an access port 12 inserted into a human brain 10 for providing access to internal brain tissue during a medical procedure, in accordance with an embodiment of the present disclosure. The access port 12 accommodates instruments, such as catheters, surgical probes, or cylindrical ports, e.g., the NICO BrainPath™. Surgical tools and instruments may then be inserted within the lumen of the access port 12 in order to perform surgical, diagnostic or therapeutic procedures, such as resecting tumors as necessary. In the example of a port-based surgery, a straight or linear access port 12 is typically guided down a sulci path of the brain. Surgical instruments would then be inserted down the access port 12. The access port 12 also facilitates use of catheters, DBS needles, a biopsy procedure, and also to biopsies and/or catheters in other medical procedures performed on other parts of the body, as well as to medical procedures that do not use an access port. Various examples of the present disclosure are generally suitable for use in any medical procedure that may use optical imaging systems.

Figure 2A:
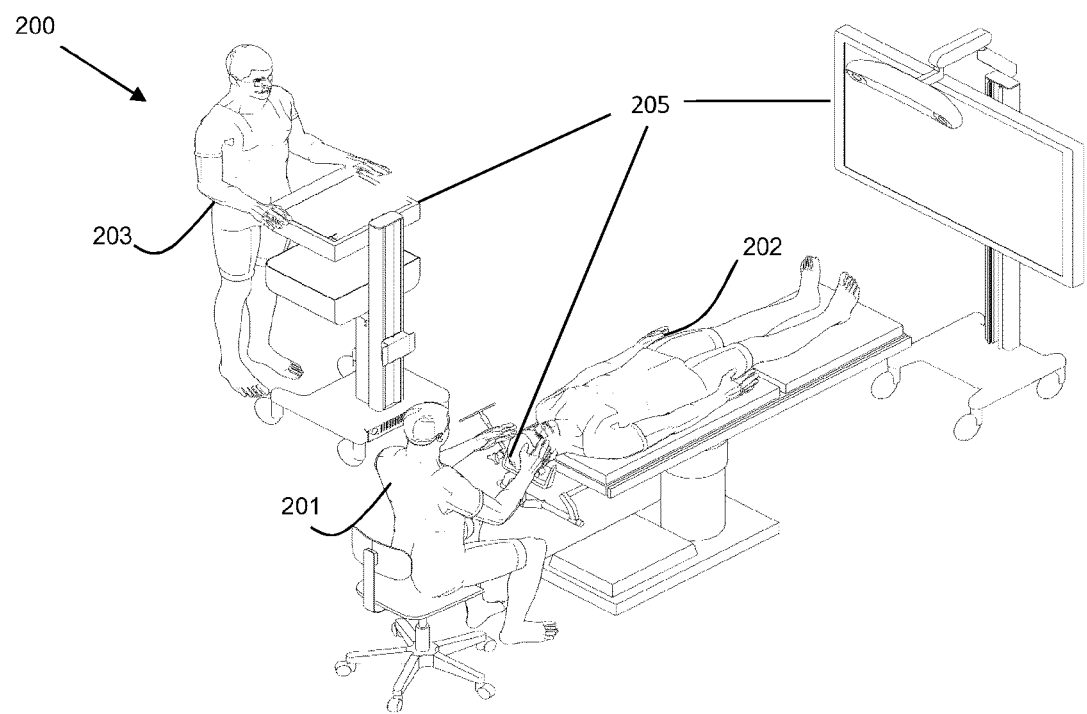
FIG. 2A is a diagram illustrating a perspective view of an example navigation system to support image guided surgery, in accordance with an embodiment of the present disclosure.

Referring to FIG. 2A, this diagram illustrates, in a perspective view, an exemplary navigation system environment 200, usable to support navigated image-guided surgery, in accordance with an embodiment of the present disclosure. A surgeon 201 performs surgery on a patient 202 in an operating room (OR) environment. A medical navigation system 205 comprises an equipment tower, tracking system, displays, and tracked instruments to assist the surgeon 201 during his procedure. An operator 203 may also be present to operate, control, and provide assistance for the medical navigation system 205.

Figure 2B:
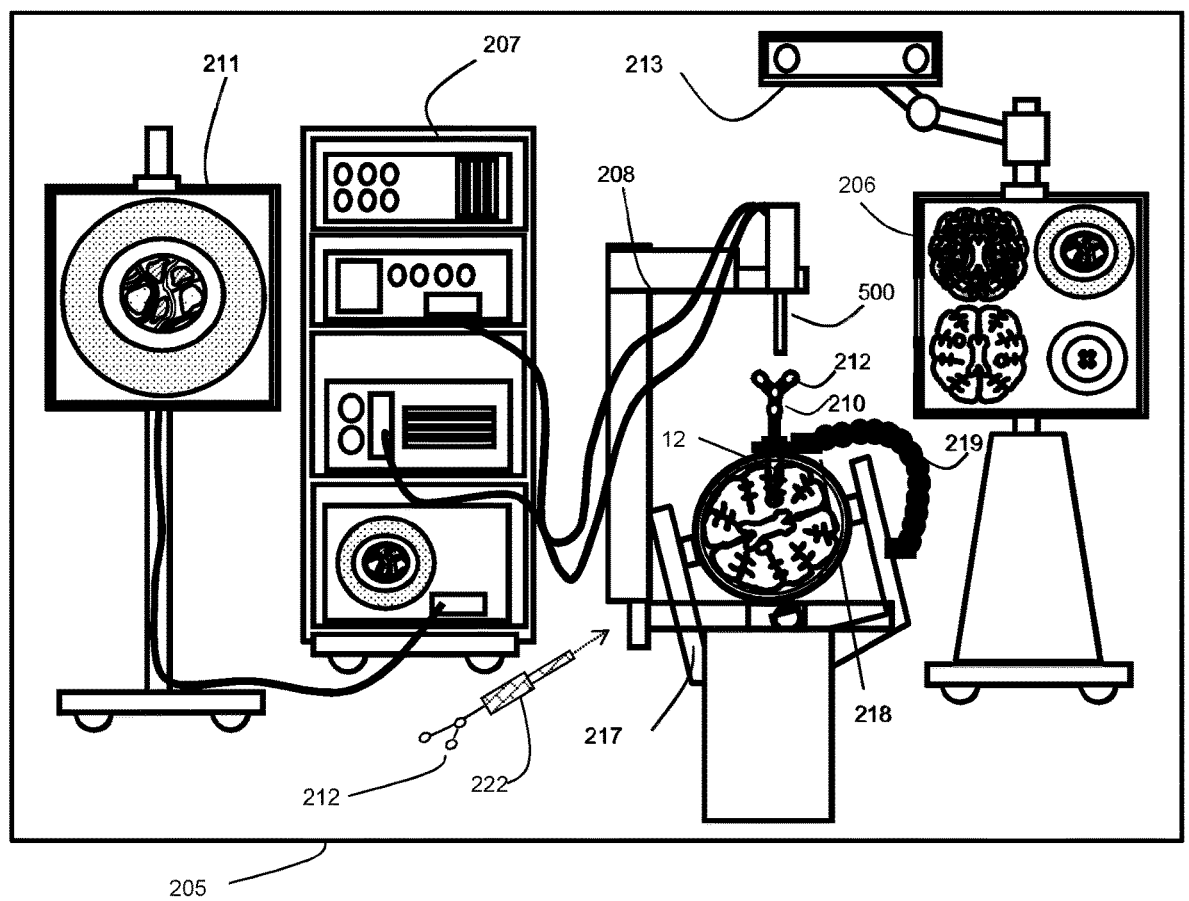
FIG. 2B is a diagram illustrating a front view of system components of an example navigation system, in accordance with an embodiment of the present disclosure.

Referring to FIG. 2B, this diagram illustrates, in a front view, an example medical navigation system 205 in greater detail, in accordance with an embodiment of the present disclosure. The disclosed optical imaging system is usable in the context of the medical navigation system 205. The medical navigation system 205 comprises at least one display, such as displays 206, 211, for displaying a video image, an equipment tower 207, and a positioning system 208, such as a mechanical arm, which may support an optical imaging system 500, e.g., comprising an optical scope. At least one of the displays 206, 211 comprises a touch-sensitive display for receiving touch input. The equipment tower 207 is mountable on a frame, e.g., a rack or cart, and may comprise a power supply and a computer or controller configured to execute at least one of planning software, navigation software, and other software for managing the positioning system 208 and at least one instrument tracked by the navigation system 205. In some examples, the equipment tower 207 comprises a single tower configuration operating with dual displays 206, 211; however, the equipment tower 207 comprises other configurations, e.g., a dual tower, a single display, etc. Further, the equipment tower 207 is configurable with a universal power supply (UPS) to provide for emergency power in addition to a regular AC adapter power supply.

Still referring to FIG. 2B, a portion of the patient's anatomy is retainable by a holder. For example, as shown, the patient's head and brain is retainable by a head holder 217. The access port 12 and associated introducer 210 are insertable into the head to provide access to a surgical site. The imaging system 500 is usable to view down the access port 12 at a sufficient magnification to allow for enhanced visibility. The output of the imaging system 500 is receivable by at least one computer or controller to generate a view that is depictable on a visual display, e.g., one or more displays 206, 211.

Still referring to FIG. 2B, in some examples, the navigation system 205 comprises a tracked pointer tool 222. The tracked pointer tool 222 comprises markers 212 to enable tracking by a tracking camera 213 and is configured to identify points, e.g., fiducial points, on a patient. An operator, typically a nurse or the surgeon 201, may use the tracked pointer tool 222 to identify the location of points on the patient 202, in order to register the location of selected points on the patient 202 in the navigation system 205. Noted is that a guided robotic system with closed loop control is usable as a proxy for human interaction. Guidance to the robotic system is providable by any combination of input sources such as image analysis, tracking of objects in the operating room using markers placed on various objects of interest, or any other suitable robotic system guidance techniques.

Still referring to FIG. 2B, fiducial markers 212 are configured to couple with the introducer 210 for tracking by the tracking camera 213, which may provide positional information of the introducer 210 from the navigation system 205. In some examples, the fiducial markers 212 are alternatively or additionally attached to the access port 12. In some examples, the tracking camera 213 comprises a 3D infrared optical tracking stereo camera, e.g., a camera comprising at least one feature of a Northern Digital Imaging™ (NDI) camera. In some examples, the tracking camera 213 alternatively comprises an electromagnetic system (not shown), such as a field transmitter, that configured to use at least one receiver coil disposed in relation to the tool(s) intended for tracking. A location of the tracked tool(s) is determinable by using the induced signals and their phases in each of the at least one receiver coil by way of a profile of the electromagnetic field (measured, calculated, or known) and a position of each at least one receiver coil relative to another at least one receiver coil (measured, calculated, or known). Operation and examples of this technology is further explained in Chapter 2 of "Image-Guided Interventions Technology and Application," Peters, T.; Cleary, K., 2008, ISBN: 978-0-387-72856-7, incorporated herein by reference in its entirety, the subject matter of which is encompassed by the present disclosure.

Still referring to FIG. 2B, location data of the positioning system 208 and/or the access port 12 is determinable by the tracking camera 213, the tracking camera 213 configured to detect the fiducial markers 212 disposed, or otherwise fixed, e.g., rigidly coupled, in relation to any of the positioning system 208, the access port 12, the introducer 210, the tracked pointer tool 222, and/or other tracked instruments. The fiducial marker(s) 212 comprise at least one of active markers and passive markers. The displays 206, 211 are configured to output the computed data of the navigation system 205. In some examples, the output provided by the displays 206, 211 comprises a multi-view output of a patient anatomy, the multi-view output comprising at least one of an axial view, a sagittal view, and a coronal view.

Still referring to FIG. 2B, at least one of the fiducial markers 212, e.g., at least one of active markers and passive markers, are placed on tools, e.g., the access port 12 and/or the imaging system 500, to be tracked, to facilitate determination of the location and orientation of such tools by using the tracking camera 213 and the navigation system 205. A stereo camera of the tracking system is configured to detect the fiducial markers 212 and to capture images thereof for providing identifiable points for tracking such tools. A tracked tool is defined by a grouping of the fiducial markers 212, whereby a rigid body is defined and identified by the tracking system. This definition, in turn, is usable for determining the position and/or orientation in 3D of a tracked tool in a virtual space. The position and orientation of the tracked tool in 3D is trackable in six degrees of freedom, e.g., x, y, and z coordinates as well as pitch, yaw, and roll rotations, and in five degrees of freedom, e.g., x, y, and z, coordinates as well as two degrees of free rotation. Preferably, the tool is tracked in at least three degrees of freedom, e.g., tracking a position of a tip of a tool in at least the x, y, and z coordinates. In use with a navigation system, at least three fiducial markers 212 are provided on a tracked tool to define the tracked tool in a virtual space; however, preferably, at least four fiducial markers 212 are used.

Still referring to FIG. 2B, camera images capturing the fiducial markers 212 are logged and tracked, by, for example, a closed circuit television (CCTV) camera. The fiducial markers 212 are selectable to enable, assist, and/or facilitate segmentation in the captured images. For example, the navigation system 205 implements infrared (IR) reflecting markers used in conjunction with an IR light source originating from the direction of the camera. An example of such an apparatus comprises tracking devices, such as the Polaris® system available from Northern Digital Inc. In some examples, the spatial position and orientation of the tracked tool and/or the actual and desired position and orientation of the positioning system 208 are determinable by optical detection using a camera. The optical detection is performable by using an optical camera, thereby rendering the fiducial markers 212 optically visible.

Still referring to FIG. 2B, in some examples, the fiducial markers 212, e.g., reflectospheres, are combinable with a suitable tracking system to determine the spatial position of the tracked tools within the operating theatre. Different tools and/or targets are providable with respect to different sets of fiducial markers 212 in different configurations. Differentiation of the different tools and/or targets and their corresponding virtual volumes is possible based on the specification configuration and/or orientation of the each set of fiducial markers 212 relative to another set of fiducial markers 212, thereby enabling each such tool and/or target to have a distinct individual identity associated with a distinct individual identifier within the navigation system 205. The distinct individual identifiers provide information to the navigation system 205, such as information relating to the size and/or shape of the tool within navigation system 205. The distinct individual identifier may also provide additional information, such as the tool's central point or the tool's central axis, among other information. The virtual tool is also determinable from a database of tools stored in, or provided to, the navigation system 205. The fiducial markers 212 are tracked relative to a reference point, or a reference object, in the operating room, such as the patient 202.

Still referring to FIG. 2B, various types of fiducial markers is used. The fiducial markers 212 may comprise the same type or a combination of at least two different types. Possible types of markers comprise reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools to which such markers are attached. Reflective adhesives, structures and patterns, glass markers, and LED markers are detectable using optical detectors, while RF and EM markers are detectable using antennas. Different marker types are selectable to suit different operating conditions. For example, using EM and RF markers enable tracking of tools without requiring a line-of-sight from a tracking camera to the fiducial markers 212; and using an optical tracking system avoids additional noise from electrical emission and detection systems.

Still referring to FIG. 2B, in some examples, the fiducial markers 212 comprise printed, or 3D, features for detection by an auxiliary camera, such as a wide-field camera (not shown) and/or the imaging system 500. Printed markers may also be used as a calibration pattern, for example to provide distance information, e.g., 3D distance information, to an optical detector. Printed identification markers comprise features, such as concentric circles with different ring spacing and/or different types of bar codes, among other features. In some examples, in addition to, or in place of, using the fiducial markers 212, the contours of objects e.g., the side of the access port 206, are captured by, and identified, using optical imaging devices and the tracking system.

Still referring to FIG. 2B, a guide clamp 218 (or, more generally, a guide) for holding the access port 12 is providable. The guide clamp 218 facilitates retention of the access port 206 at a fixed position and orientation, thereby freeing use of the surgeon's hands. An articulated arm 219 is provided to hold the guide clamp 218. The articulated arm 219 has up to six degrees of freedom for positioning the guide clamp 218. The articulated arm 219 is lockable to fix its position and orientation, e.g., once a desired position is achieved. The articulated arm 219 is attached, or attachable, in relation to a point based on the patient head holder 217, or another suitable point, such as on another patient support, e.g., on the surgical bed, to ensure that, when locked in place, the guide clamp 218 does not move relative to the patient's head.

Still referring to FIG. 2B, in a surgical operating room (or theatre), setup of a navigation system is relatively complex, e.g., many pieces of equipment associated with the surgical procedure, as well as elements of the navigation system 205, must be arranged and/or prepared. Further, setup time typically increases as more equipment is added. To assist in addressing this, the navigation system 205 comprises two additional wide-field cameras to enable video overlay information. Video overlay information is then be insertable into displayed images, such as images displayed on at least one of the displays 206, 211. The overlay information represents the physical space where accuracy of the 3D tracking system, e.g., a part of the navigation system, is greater, represents the available range of motion of the positioning system 208 and/or the imaging system 500, and/or may facilitates guiding the head and/or positioning the patient.

Still referring to FIG. 2B, the navigation system 205 provides tools to the neurosurgeon that may help to provide more relevant information to the surgeon, and may assist in improving performance and accuracy of port-based neurosurgical operations. Although described in the present disclosure in the context of port-based neurosurgery, e.g., for removal of brain tumors and/or for treatment of intracranial hemorrhages (ICH), the navigation system 205 is also suitable for at least one of: a brain biopsy, a functional/deep-brain stimulation, a catheter/shunt placement (in the brain or elsewhere), an open craniotomy, and/or an endonasal/skull-based/ear-nose-throat (ENT) procedure, among others. The same navigation system 205 is usable for performing any or all of these procedures, with, or without, modification as appropriate.

Still referring to FIG. 2B, although the present disclosure may discuss the navigation system 205 in the context of neurosurgery, the navigation system 205, for example, is usable for performing a diagnostic procedure, such as brain biopsy. A brain biopsy may involve the insertion of a thin needle into a patient's brain for purposes of removing a sample of brain tissue. The brain tissue is subsequently assessed by a pathologist to determine whether the brain tissue is cancerous, for example. Brain biopsy procedures are conducted with, or without, a stereotactic frame. Both types of procedures are performable using image-guidance. Frameless biopsies, in particular, are performable by way of the navigation system 205.

Still referring to FIG. 2B, in some examples, the tracking camera 213 is adaptable to any suitable tracking system. In some examples, the tracking camera 213, and any associated tracking system that uses the tracking camera 213, is replaceable with any suitable tracking system which may, or may not, use camera-based tracking techniques. For example, a tracking system that does not use the tracking camera 213, such as a radiofrequency tracking system, is used with the navigation system 205.

Figure 3:
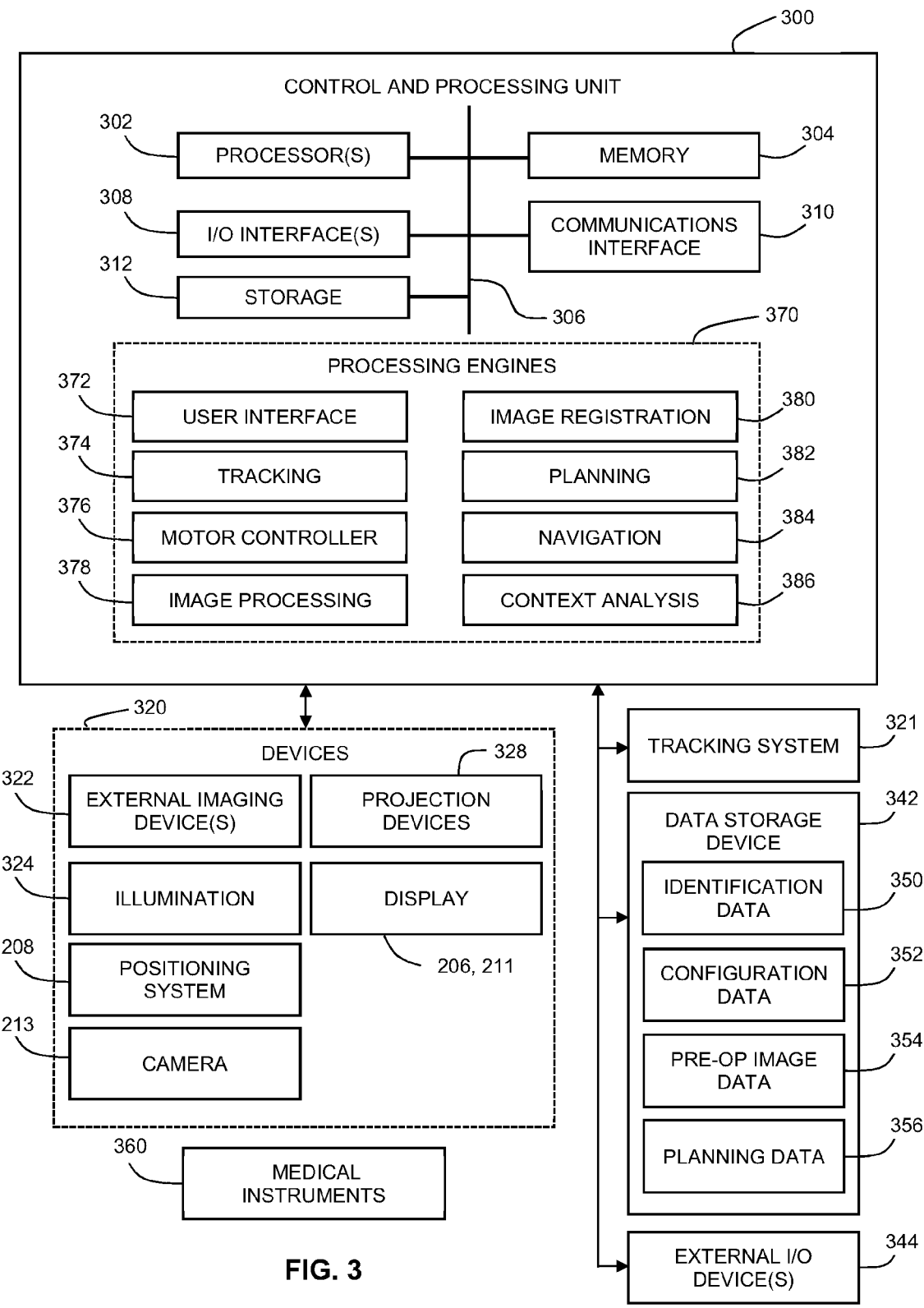
FIG. 3 is a block diagram illustrating an example control and processing system usable with the example navigation systems, as shown in FIGS. 2A and 2B, in accordance with an embodiment of the present disclosure.

Referring to FIG. 3, this block diagram illustrates a control and processing system 300 usable in the medical navigation system 205, as shown in FIG. 2B, e.g., as part of the equipment tower 207, in accordance with an embodiment of the present disclosure. In one example, the control and processing system 300 comprises at least one processor 302, a memory 304, a system bus 306, at least one input/output (I/O) interface 308, a communications interface 310, and a storage device 312. The control and processing system 300 is interfaceable with other external devices, such as a tracking system 321, a data storage 342, and at least one external user I/O device 344, e.g., at least one of a display, a keyboard, a mouse, sensors attached to medical equipment, a foot pedal, a microphone, and a speaker.

Still referring to FIG. 3, the data storage 342 comprises any suitable data storage device, such as a local, or remote, computing device, e.g. a computer, hard drive, digital media device, or server, having a database stored thereon. The data storage device 342 further comprises identification data 350 for identifying one or more medical instruments 360 and configuration data 352 that associates customized configuration parameters with one or more medical instruments 360. The data storage device 342 further comprises preoperative image data 354 and/or medical procedure planning data 356. Although the data storage device 342 is shown as a single device, understood is that, in other embodiments, the data storage device 342 alternatively comprises multiple storage devices.

Still referring to FIG. 3, the medical instruments 360 are identifiable by the control and processing unit 300. The medical instruments 360 are connected to, and controlled by, the control and processing unit 300. Alternatively, the medical instruments 360 are operated, or otherwise employed, independent of the control and processing unit 300. The tracking system 321 is employed to track at least one medical instrument 360 and spatially register the at least one tracked medical instrument to an intraoperative reference frame. For example, a medical instrument 360 comprises tracking markers, such as tracking spheres, recognizable by the tracking camera 213. In one example, the tracking camera 213 comprises an infrared (IR) tracking camera. In another example, a sheath placed over a medical instrument 360 is connected to, and controlled by, the control and processing unit 300.

Still referring to FIG. 3, the control and processing unit 300 is also interfaceable with a number of configurable devices 320, and can intraoperatively reconfigure at least one such device based on configuration parameters obtained from configuration data 352. Examples of devices 320, include, but are not limited to, at least one external imaging device 322, at least one illumination device 324, the positioning system 208, the tracking camera 213, at least one projection device 328, and at least one display, such as the displays 206, 211.

Still referring to FIG. 3, exemplary aspects of the embodiments are implementable via the processor(s) 302 and/or memory 304, in accordance with the present disclosure. For example, the functionalities described herein can be partially implemented via hardware logic in the processor 302 and partially using the instructions stored in the memory 304, as at least one processing module or engine 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are separately shown in FIG. 3, in some examples, the processing modules 370 are storable in the memory 304; and the processing modules 370 are collectively referred as processing modules 370. In some examples, at least two modules 370 are used together for performing a function. Although depicted as separate modules 370, the modules 370 is embodied as a unified set of computer-readable instructions, e.g., stored in the memory 304, rather than as distinct sets of instructions.

Still referring to FIG. 3, understood is that the system 300 is not intended to be limited to the components shown in FIG. 3. One or more components of the control and processing system 300 are provided as an external component or device. In one example, the navigation module 384 is provided as an external navigation system that is integrated with the control and processing system 300. Some embodiments is implemented using the processor 302 without additional instructions stored in memory 304. Some embodiments are implemented using the instructions stored in memory 304 for execution by one or more general purpose microprocessors. Thus, the present disclosure is not limited to any specific configuration of hardware and/or software.

Still referring to FIG. 3, in some examples, the navigation system 205, which may include the control and processing unit 300, provides tools to the surgeon for improving performance of the medical procedure and/or post-operative outcomes. In addition to removal of brain tumours and intracranial hemorrhages (ICH), the navigation system 205 is also applicable to a brain biopsy, a functional/deep-brain stimulation, a catheter/shunt placement procedure, open craniotomies, endonasal/skull-based/ENT, spine procedures, and other parts of the body, such as breast biopsies, liver biopsies, etc. While several examples have been provided, examples of the present disclosure are applied to any suitable medical procedure.

Figure 4A:
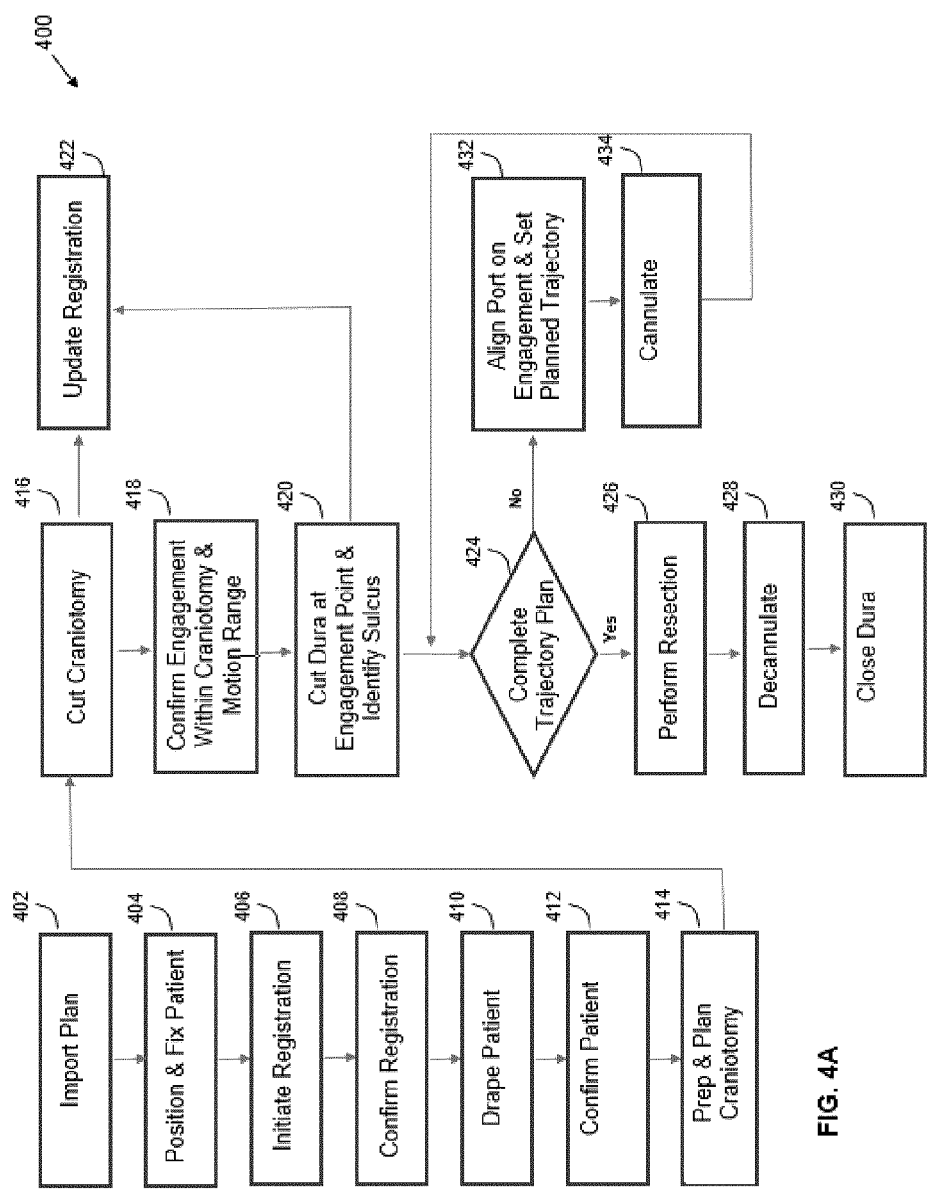
FIG. 4A is a flow diagram illustrating an example method involving a surgical procedure implementable using the example navigation systems, as shown in FIGS. 2A and 2B, in accordance with an embodiment of the present disclosure.

Referring to FIG. 4A, this flow diagram illustrates a method 400 of performing a port-based surgical procedure using a navigation system, such as the medical navigation system 205, as described in relation to FIGS. 2A and 2B, in accordance with an embodiment of the present disclosure. The method 400 comprises importing a port-based surgical plan, as indicated by block 402. Once the plan has been imported into the navigation system at the block 402, the method 400 further comprises positioning and fixing the patient by using a body holding mechanism and confirming that the head position complies with the patient plan in the navigation system, as indicated by block 404, wherein confirming that the head position complies with the patient plan is implementable by a computer or a controller being a component of the equipment tower 207. The method 400 further comprises initiating registration of the patient, as indicated by block 406. The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 4A, appreciated is that numerous registration techniques are available and at least one of the techniques is applied to the present example, in accordance with embodiments of the present disclosure. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images is co-registered, while multi-modality registration methods are used to register images acquired by different scanner or sensor types, for example in magnetic resonance imaging (MRI) and positron emission tomography (PET). In the present disclosure, multi-modality registration methods are used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
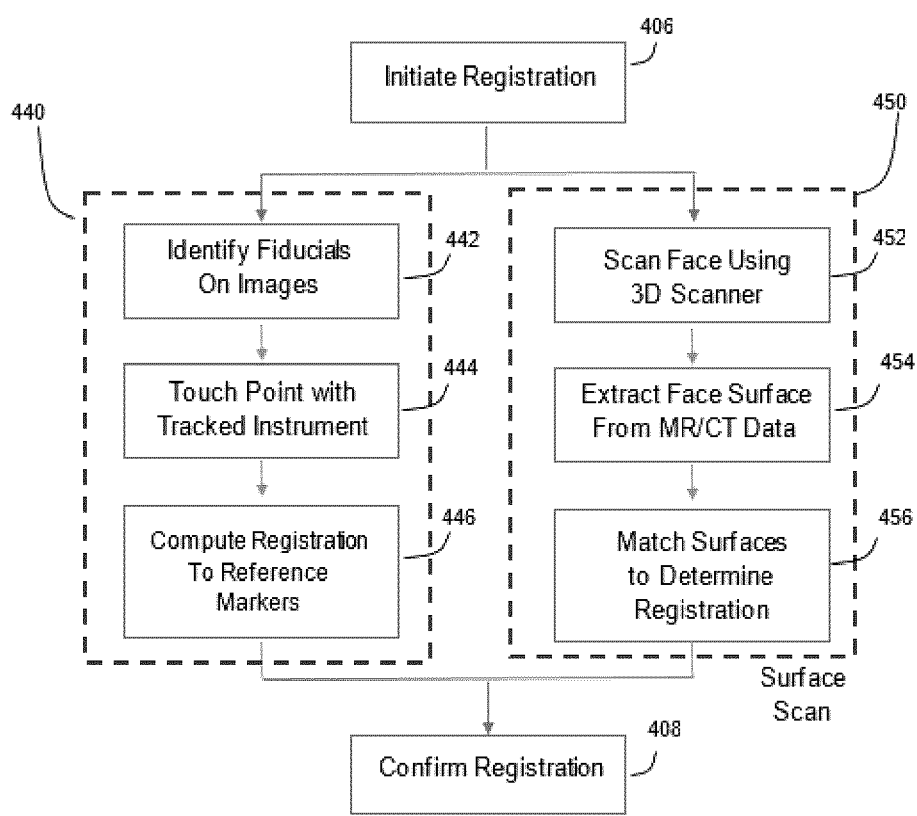
FIG. 4B is a flow diagram illustrating an example method of registering a patient for a surgical procedure, as shown in FIG. 4A, in accordance with an embodiment of the present disclosure.

Referring to FIG. 4B, this flow diagram illustrates an example of alternate sets of steps performable between performing the step of initiating registration, as indicated by block 406, and performing the step of completing registration, as indicated by block 408, in the method 400, as shown in FIG. 4A, in accordance with embodiments of the present disclosure. If the use of fiducial touch points is contemplated, after the step of initiating registration, as indicated by block 406, the method 400 comprises performing a first alternate set of steps, as indicated by block 440, the first alternative set of steps comprising: identifying fiducial markers 112 on images, as indicated by block 442; touching the touch points with a tracked instrument, as indicated by block 444; and computing the registration to the reference markers by way of the navigation system 205, as indicated by block 446. However, if the use of a surface scan is contemplated, after the step of initiating registration, as indicated by block 406, the method 400 comprises performing a second alternate set of steps, as indicated by block 450, the second alternative set of steps comprising: scanning the face by using a 3D scanner, as indicated by block 452; extracting the face surface from MR/CT data, as indicated by block 454; and matching surfaces to determine registration data points, as indicated by block 456. Upon completion of either the first alternate set of steps, as indicated by block 440, or the second alternate set of steps, as indicated by block 450, the method 400 further comprises confirming registration by using the extracted data extracted and processing the same, as indicated by block 408, as also shown in FIG. 4A.

Referring back to FIG. 4A, once registration is confirmed, as indicated by block 408, the method 400 further comprises draping the patient, as indicated by block 410. Typically, draping comprises covering the patient and surrounding areas with a sterile barrier to create and maintain a sterile field during the surgical procedure. The purpose of draping is to eliminate the passage of microorganisms, e.g., bacteria, viruses, prions, contamination, and the like, between non-sterile and sterile areas. At this point, conventional navigation systems require that the non-sterile patient reference is replaced with a sterile patient reference of identical geometry location and orientation.

Still referring back to FIG. 4A, upon completion of draping, as indicated by block 410, the method 400 further comprises: confirming the patient engagement points, as indicated by block 412; and preparing and planning the craniotomy, as indicated by block 414. Upon completion of the preparation and planning of the craniotomy, as indicated by block 414, the method 400 further comprises: performing the craniotomy by cutting a bone flap and temporarily removing the same from the remainder of the skull to access the brain, as indicated by block 416; and updating registration data with the navigation system, as indicated by block 422. Next, the method 400 further comprises: confirming engagement and the motion range within region of the craniotomy, as indicated by block 418; and cutting the dura at the engagement points and identifying the sulcus, as indicated by block 420.

Still referring back to FIG. 4A, the method 400 further comprises determining whether the trajectory plan has been completed, as indicated by block 424. If the trajectory plan is not yet completed, the method 400 further comprises: aligning a port on engagement and setting the planned trajectory, as indicated by block 432; and cannulating, as indicated by block 434; and determining whether the trajectory plan is completed, as indicated by block 424. Cannulation involves inserting a port into the brain, typically along a sulci pat, the sulci path being identified in performing the step of cutting the dura at the engagement points and identifying the sulcus, as indicated by block 420, along a trajectory plan. Further, cannulation is typically an iterative process that involves repeating the steps of aligning the port on engagement and setting the planned trajectory, as indicated by block 432, and then cannulating to the target depth, as indicated by block 434, until the complete trajectory plan is executed by making such determination, as indicated by block 424.

Still referring back to FIG. 4A, the method 400 further comprises determining whether the trajectory plan has been completed, as indicated by block 424. If the trajectory plan is completed, the method 400 further comprises: performing a resection to remove part of the brain and/or tumor of interest, as indicated by block 426; decannulating by removing the port and any tracking instruments from the brain, as indicated by block 428; and closing the dura and completing the craniotomy, as indicated by block 430. Some aspects of the steps shown in FIG. 4A are specific to port-based surgery, such as portions of the steps indicated by blocks 428, 420, and 434, but the appropriate portions of these blocks is skipped or suitably modified when performing non-port based surgery.

Referring back to both FIGS. 4A and 4B, when performing a surgical procedure using a medical navigation system 205, the medical navigation system 205 may acquire and maintain a reference of the location of the tools in use as well as the patient in three-dimensional (3D) space. In other words, during a navigated neurosurgery, a tracked reference frame that is fixed, e.g., relative to the patient's skull, is present. During the registration phase of a navigated neurosurgery, e.g., in performing the step indicated by block 406, a transformation is calculated that maps the frame of reference from preoperative MRI or CT imagery to the physical space of the surgery, specifically the patient's head. This is accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established, e.g., by performing the step as indicated by block 410.

Referring to FIG. 5, this diagram illustrates, in a perspective view, use of an example imaging system 500, in a medical procedure, in accordance with an embodiment of the present disclosure. Although FIG. 5 shows the imaging system 500 being used in the context of a navigation system environment 200, e.g., using a navigation system as above described, the imaging system 500 may also be used outside of a navigation system environment, e.g., without any navigation support. An operator, typically a surgeon 201, may use the imaging system 500 to observe the surgical site, e.g., to look down an access port. The imaging system 500 is attached to a positioning system 208, e.g., a controllable and adjustable robotic arm. The position and orientation of the positioning system 208, imaging system 500 and/or access port is tracked using a tracking system, such as described for the navigation system 205. The distance d between the imaging system 500 (more specifically, the aperture of the imaging system 500) and the viewing target, e.g., the surface of the surgical site, is referred to as the WD. The imaging system 500 is configurable for use in a predefined range of WD, e.g., in the range of approximately 15 cm to approximately 75 cm. Noted is that, if the imaging system 500 is mounted on the positioning system 208, the actual available range of WD is dependent on both the WD of the imaging system 500 as well as the workspace and kinematics of the positioning system 208.

Figure 6:
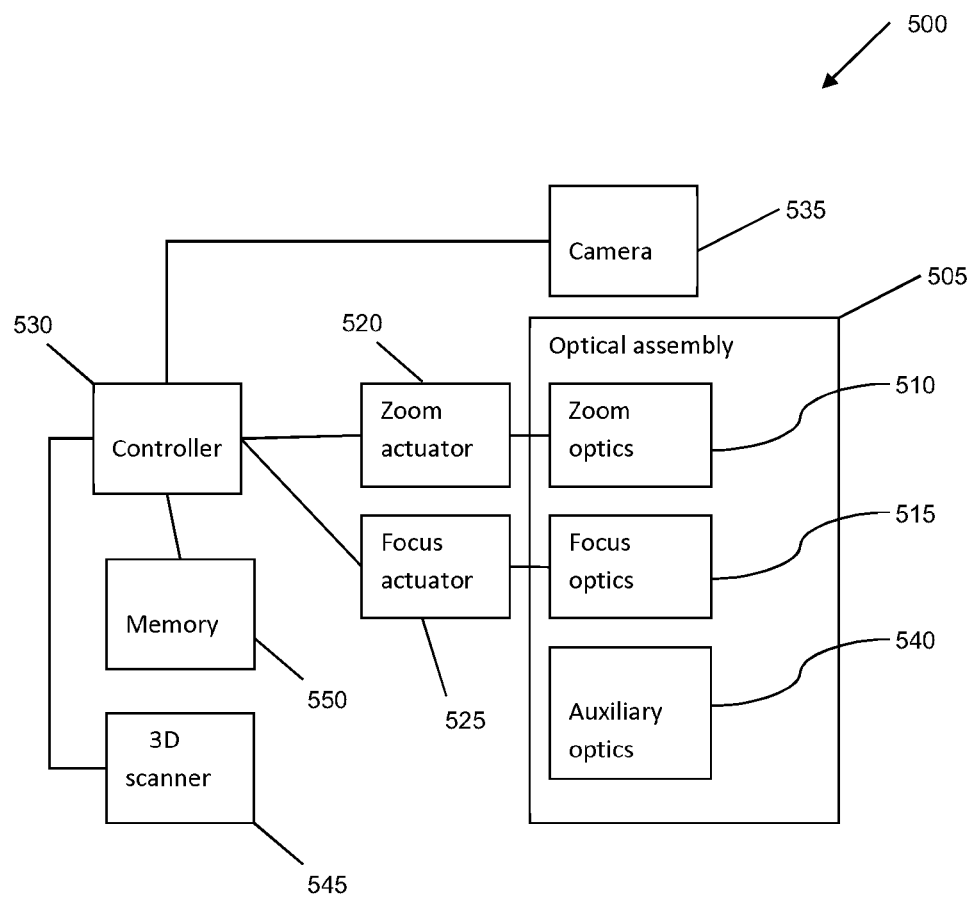
FIG. 6 is a block diagram illustrating an example optical imaging system, in accordance with an embodiment of the present disclosure.

Referring to FIG. 6, this block diagram illustrates components of an example imaging system 500, in accordance with an embodiment of the present disclosure. The imaging system 500 comprises an optical assembly 505 (also referred to as an optical train). The optical assembly 505 comprises optics, e.g., lenses, optical fibers, etc., for focusing and zooming on the viewing target. The optical assembly 505 comprises zoom optics 510 (which may include one or more zoom lenses) and focus optics 515 (which may include one or more focus lenses). Each of the zoom optics 510 and the focus optics 515 are independently movable within the optical assembly 505 in order to respectively adjust the zoom and focus. Where the zoom optics 510 and/or the focus optics 515 comprise more than one lens, each individual lens is independently movable. The optical assembly 505 comprises an aperture (not shown) which is adjustable.

Still referring to FIG. 6, the imaging system 500 comprises a zoom actuator 520 and a focus actuator 525 for respectively positioning the zoom optics 510 and the focus optics 515. The zoom actuator 520 and/or the focus actuator 525 comprise an electric motor or other types of actuators, such as pneumatic actuators, hydraulic actuators, shape-changing materials, e.g., piezoelectric materials or other smart materials, or engines, among other possibilities. Although the term "motorized" is used in the present disclosure, understood is that the use of this term does not limit the present disclosure to use of motors necessarily, but is intended to cover all suitable actuators, including motors. Although the zoom actuator 520 and the focus actuator 525 are shown outside of the optical assembly 505, in some examples, the zoom actuator 520 and the focus actuator 525 are components of, or are integrated with, the optical assembly 505. The zoom actuator 520 and the focus actuator 525 may operate independently, to respectively control positioning of the zoom optics 510 and the focus optics 515. The lens(es) of the zoom optics 510 and/or the focus optics 515 is each mounted on a linear stage, e.g., a motion system that restricts an object to move in a single axis, which may include a linear guide and an actuator; or a conveyor system such as a conveyor belt mechanism, that is respectively moved by the zoom actuator 520 and/or the focus actuator 525 to control positioning of the zoom optics 510 and/or the focus optics 515. In some examples, the zoom optics 510 is mounted on a linear stage that is driven, via a belt drive, by the zoom actuator 520, while the focus optics 515 is geared to the focus actuator 525. The independent operation of the zoom actuator 520 and the focus actuator 525 may enable the zoom and focus to be adjusted independently. Thus, when an image is in focus, the zoom is adjusted without requiring further adjustments to the focus optics 515 to produce a focused image.

Still referring to FIG. 6, operation of the zoom actuator 520 and the focus actuator 525 is controllable by a controller 530, e.g., a microprocessor, of the imaging system 500. The controller 530 may receive control input, e.g., from an external system, such as an external processor or an input device. The control input may indicate a desired zoom and/or focus, and the controller 530 may in response cause the zoom actuator 520 and/of focus actuator 525 to move the zoom optics 510 and/or the focus optics 515 accordingly to achieve the desired zoom and/or focus. In some examples, the zoom optics 510 and/or the focus optics 515 is moved or actuated without the use of the zoom actuator 520 and/or the focus actuator 525. For example, the focus optics 515 uses electrically-tunable lenses or other deformable material that is directly controllable by the controller 530.

Still referring to FIG. 6, by providing the controller 530, the zoom actuator 520 and the focus actuator 525 all as part of the imaging system 500, the imaging system 500 may enable an operator, e.g., a surgeon, to control zoom and/or focus during a medical procedure without having to manually adjust the zoom and/or focus optics 510, 515. For example, the operator may provide control input to the controller 530 verbally, e.g., via a voice recognition input system, by instructing an assistant to enter control input into an external input device, e.g., into a user interface provided by a workstation, using a foot pedal, or by other such means. In some examples, the controller 530 executes preset instructions to maintain the zoom and/or focus at preset values, e.g., to perform autofocusing, without requiring further control input during the medical procedure.

Still referring to FIG. 6, an external processor, e.g., a processor of a workstation or the navigation system, in communication with the controller 530 is used to provide control input to the controller 530. For example, the external processor provides a graphical user interface via which the operator or an assistant input instructions to control zoom and/or focus of the imaging system 500. The controller 530 is alternatively or additionally in communication with an external input system, e.g., a voice-recognition input system or a foot pedal. The optical assembly 505 comprises at least one auxiliary optic 540, e.g., an adjustable aperture, which is static or dynamic. Where the auxiliary optics 540 is dynamic, the auxiliary optics 540 is moved using an auxiliary actuator (not shown) which is controlled by the controller 530.

Still referring to FIG. 6, the imaging system 500 further comprises a camera 535, e.g., a high-definition (HD) camera, configured to capture image data from the optical assembly. Operation of the camera is controlled by the controller 530. The camera 535 also outputs data to an external system, e.g., an external workstation or external output device, to view the captured image data. In some examples, the camera 535 outputs data to the controller 530, which, in turn, transmits the data to an external system for viewing. By providing image data to an external system for viewing, the captured images are viewable on a larger display and are displayable together with other information relevant to the medical procedure, e.g., a wide-field view of the surgical site, navigation markers, 3D images, etc. The camera 535 used with the imaging system 500 facilitates improving the consistency of image quality among different medical centers. Image data captured by the camera 535 is displayable on a display together with a wide-field view of the surgical site, for example, in a multiple-view user interface. The portion of the surgical site that is captured by the camera 535 is visually indicated in the wide-field view of the surgical site.

Still referring to FIG. 6, the imaging system 500 comprises a three-dimensional (3D) scanner 545 or 3D camera for obtaining 3D information of the viewing target. 3D Information from the 3D scanner 545 is also captured by the camera 535, or is captured by the 3D scanner 545, itself. Operation of the 3D scanner 545 is controlled by the controller 530; and the 3D scanner 545 transmits data to the controller 530. In some examples, the 3D scanner 545, itself, transmits data to an external system, e.g., an external work station. 3D information from the 3D scanner 545 is used to generate a 3D image of the viewing target, e.g., a 3D image of a target tumor to be resected). 3D information is also useful in an augmented reality (AR) display provided by an external system. For example, an AR display, e.g., provided via AR glasses, may, using information from a navigation system to register 3D information with optical images, overlay a 3D image of a target specimen on a real-time optical image, e.g., an optical image captured by the camera 535.

Still referring to FIG. 6, the controller 530 is coupled to a memory 550. The memory 550 is internal or external in relation to the imaging system 500. Data received by the controller 530, e.g., image data from the camera 535 and/or 3D data from the 3D scanner, is stored in the memory 550. The memory 550 may also contain instructions to enable the controller to operate the zoom actuator 520 and the focus actuator 525. For example, the memory 550 stores instructions to enable the controller to perform autofocusing, as further below discussed. The imaging system 500 communicates with an external system, e.g., a navigation system or a workstation, via wired or wireless communication. In some examples, the imaging system 500 comprises a wireless transceiver (not shown) to enable wireless communication. In some examples, the imaging system 500 comprises a power source, e.g., a battery, or a connector to a power source, e.g., an AC adaptor. In some examples, the imaging system 500 receives power via a connection to an external system, e.g., an external workstation or processor.

Still referring to FIG. 6, in some examples, the imaging system 500 comprises a light source (not shown). In some examples, the light source may not itself generate light but rather direct light from another light generating component. For example, the light source comprises an output of a fibre optics cable connected to another light generating component, which is part of the imaging system 500 or external to the imaging system 500. The light source is mounted near the aperture of the optical assembly, to direct light to the viewing target. Providing the light source with the imaging system 500 may help to improve the consistency of image quality among different medical centers. In some examples, the power or output of the light source is controlled by the imaging system 500, e.g., by the controller 530, or is controlled by a system external to the imaging system 500, e.g., by an external workstation or processor, such as a processor of a navigation system.

Still referring to FIG. 6, in some examples, the optical assembly 505, zoom actuator 520, focus actuator 525, and camera 535 may all be housed within a single housing (not shown) of the imaging system. In some examples, the controller 530, memory 550, 3D scanner 545, wireless transceiver, power source, and/or light source are also housed within the housing. In some examples, the imaging system 500 also provides mechanisms to enable manual adjusting of the zoom and/or focus optics 510, 515. Such manual adjusting is enabled in addition to motorized adjusting of zoom and focus. In some examples, such manual adjusting is enabled in response to user selection of a "manual mode" on a user interface.

Still referring to FIG. 6, the imaging system 500 is mountable on a movable support structure, such as the positioning system, e.g., robotic arm, of a navigation system, a manually operated support arm, a ceiling mounted support, a movable frame, or other such support structure. The imaging system 500 is removably mounted on the movable support structure. In some examples, the imaging system 500 comprises a support connector, e.g., a mechanical coupling, to enable the imaging system 500 to be quickly and easily mounted or dismounted from the support structure. The support connector on the imaging system 500 is configured to be suitable for connecting with a typical complementary connector on the support structure, e.g., as designed for typical end effectors. In some examples, the imaging system 500 is mounted to the support structure together with other end effectors, or is mounted to the support structure via another end effector.

Still referring to FIG. 6, when mounted, the imaging system 500 is at a known fixed position and orientation relative to the support structure, e.g., by calibrating the position and orientation of the imaging system 500 after mounting. In this way, by determining the position and orientation of the support structure, e.g., using a navigation system or by tracking the movement of the support structure from a known starting point), the position and orientation of the imaging system 500 is also determined. In some examples, the imaging system 500 may include a manual release button that, when actuated, enable the imaging system 500 to be manually positioned, e.g., without software control by the support structure.

Still referring to FIG. 6, in some examples, where the imaging system 500 is intended to be used in a navigation system environment, the imaging system 500 comprises an array of trackable markers, which is mounted on a frame on the imaging system 500 to enable the navigation system to track the position and orientation of the imaging system 500. Alternatively or additionally, the movable support structure, e.g., a positioning system of the navigation system, on which the imaging system 500 is mounted, is tracked by the navigation system; and the position and orientation of the imaging system 500 is determined by using the known position and orientation of the imaging system 500 relative to the movable support structure.

Still referring to FIG. 6, the trackable markers comprise passive reflective tracking spheres, active infrared (IR) markers, active light emitting diodes (LEDs), a graphical pattern, or a combination thereof. At least three trackable markers are provided on a frame to enable tracking of position and orientation. In some examples, four passive reflective tracking spheres are coupled to the frame. While some specific examples of the type and number of trackable markers have been given, any suitable trackable marker and configuration may be used, as appropriate.

Still referring to FIG. 6, determination of the position and orientation of the imaging system 500 relative to the viewing target is performed by a processor external to the imaging system 500, e.g., a processor of the navigation system. Information about the position and orientation of the imaging system 500 is used, together with a robotic positioning system, to maintain alignment of the imaging system 500 with the viewing target, e.g., to view down an access port during port-based surgery, throughout the medical procedure.

Still referring to FIG. 6, for example, the navigation system tracks the position and orientation of the positioning system and/or the imaging system 500 either collectively or independently. Using this information as well as tracking of the access port, the navigation system determines the desired joint positions for the positioning system so as to maneuver the imaging system 500 to the appropriate position and orientation to maintain alignment with the viewing target, e.g., the longitudinal axes of the imaging system 500 and the access port being aligned. This alignment is maintained throughout the medical procedure automatically, without requiring explicit control input. In some examples, the operator is able to manually move the positioning system and/or the imaging system 500, e.g., after actuation of a manual release button. During such manual movement, the navigation system continues to track the position and orientation of the positioning system and/or the imaging system 500. After completion of manual movement, the navigation system, e.g., in response to user input, such as using a foot pedal, indicating that manual movement is complete, reposition and reorient the positioning system and the imaging system 500 to regain alignment with the access port.

Still referring to FIG. 6, the controller 530 uses information about the position and orientation of the imaging system 500 to perform autofocusing. For example, the controller 530 determines the WD between the imaging system 500 and the viewing target; and, thus, determine the desired positioning of the focus optics 515, e.g., using appropriate equations to calculate the appropriate positioning of the focus optics 515 to achieve a focused image, and move the focus optics 515, using the focus actuator 525, in order to bring the image into focus. For example, the position of the viewing target is determined by a navigation system. The WD is determined by the controller 530 using information, e.g., received from the navigation system, from the positioning system or other external system, about the position and orientation of the imaging system 500 and/or the positioning system relative to the viewing target. In some examples, the WD is determined by the controller 530 using an infrared light (not shown) mounted on near the distal end of the imaging system 500.

Still referring to FIG. 6, in some examples, the controller 530 may perform autofocusing without information about the position and orientation of the imaging system 500. For example, the controller 530 controls the focus actuator 525 to move the focus optics 515 into a range of focus positions and control the camera 535 to capture image data at each focus position. The controller 530 may then perform image processing on the captured images to determine which focus position has the sharpest image and determine this focus position to be the desired position of the focus optics 515. The controller 530 then controls the focus actuator 525 to move the focus optics 515 to the desired position. Any other autofocus routine, such as those suitable for handheld cameras, is implemented by the controller 530 as appropriate.

Still referring to FIG. 6, in some examples, the viewing target is dynamically defined by the surgeon, e.g., using a user interface provided by a workstation, by touching the desired target on a touch-sensitive display, by using eye or head tracking to detect a point at which the surgeon's gaze is focused and/or by voice command; and the imaging system 500 performs autofocusing to dynamically focus the image on the defined viewing target, thereby enabling the surgeon to focus an image on different points within a FoV, without changing the FoV, and without having to manually adjust the focus of the imaging system 500. Autofocusing is performable by way of a surgeon or, alternatively, by way of the controller 530.

Still referring to FIG. 6 and ahead to FIG. 11, in some examples, the imaging system 500 is configured to perform autofocusing relative to an instrument being used in the medical procedure. An example of this feature is shown in FIG. 11. For example, the position and orientation of a medical instrument, such as a tracked pointer tool 222, is determined; and the controller 530 performs autofocusing to focus the captured image on a point defined relative to the medical instrument. In the examples shown in FIG. 11, the tracked pointer tool 222 has a defined focus point at the distal tip of the pointer 222. As the tracked pointer tool 222 is moved, the WD between the optical imaging system 500 and the defined focus point (at the distal tip of the tracked pointer tool 222) changes (from D1 in the left image to D2 in the right image, for example). The autofocusing is performed in a manner similar to that as above described; however, instead of autofocusing on a viewing target in the surgical field, the imaging system 500 focuses on a focus point that is defined relative to the medical instrument. The medical instrument is used in the surgical field to guide the imaging system 500 to autofocus on different points in the surgical field, as below discussed, thereby enabling a surgeon to change the focus within a FoV, e.g., focus on a point other than at the center of the FoV, without changing the FoV, and without needing to manually adjust the focus of the imaging system 500. Where the FoV includes objects at different depths, the surgeon uses the medical instrument, e.g., a pointer, to indicate to the imaging system 500 the object and/or depth desired for autofocusing.

Still referring to FIG. 6, for example, the controller 530 may receive information about the position and orientation of a medical instrument. This position and orientation information is received from an external source, e.g., from an external system tracking the medical instrument or from the medical instrument itself, or is received from another component of the imaging system 500, e.g., an infrared sensor or a machine vision component of the imaging system 500. The controller 530 may determine a focus point relative to the position and orientation of the medical instrument. The focus point is predefined for a given medical instrument, e.g., the distal tip of a pointer, the distal end of a catheter, the distal end of an access port, the distal end of a soft tissue resector, the distal end of a suction, the target of a laser, or the distal tip of a scalpel), and is different for different medical instruments. The controller 530 may use this information, together with information about the known position and orientation of the imaging system 500, e.g., determined as discussed above, in order to determine the desired position of the focus optics 515 to achieve an image focused on the focus point defined relative to the medical instrument.

Still referring to FIG. 6, in examples where the imaging system 500 is used with a navigation system 205 (see FIG. 2B), the position and orientation of a medical instrument, e.g., a tracked pointer tool 222 or a tracked port 210, is tracked and determined by the navigation system 205. The controller 530 of the imaging system 500 automatically autofocuses the imaging system 500 to a predetermined point relative to the tracked medical instrument, e.g., autofocus on the tip of the tracked pointer tool 222 or on the distal end of the access port 210. Autofocusing is performed relative to other medical instruments and other tools that are used in the medical procedure.

Still referring to FIG. 6, in some examples, the imaging system 500 is configured to perform autofocusing relative to a medical instrument only when a determination is made that the focus point relative to the medical instrument is within the FoV of the imaging system 500 is determined, whereby an unintentional change of focus is avoidable when a medical instrument is moved in the vicinity of but outside the FoV of the imaging system 500. In examples where the imaging system 500 is mounted on a movable support system, e.g., a robotic arm, if the focus point of the medical instrument is outside of the current FoV of the imaging system 500, the movable support system positions and orients the imaging system 500 to bring the focus point of the medical instrument within the FoV of the imaging system 500, in response to input, e.g., in response to user command via a user interface or voice input, or via activation of a foot pedal.

Still referring to FIG. 6, the imaging system 500 is configured to implement a small time lag before performing autofocus relative to a medical instrument in order to avoid erroneously changing focus while the focus point of the medical instrument is brought into, and out of, the FoV. For example, the imaging system 500 is configured to autofocus on the focus point only after the focus point has been substantially stationary for a predetermined length of time, e.g., approximately 0.5 s to approximately 1 s. In some examples, the imaging system 500 is also configured to perform zooming with the focus point as the zoom center. For example, while a focus point is in the FoV, or after autofocusing on a certain point in the FoV, the user may provide command input, e.g., via a user interface, voice input or activation of a foot pedal, to instruct the imaging system 500 to zoom in on the focus point. The controller 530 then positions the zoom optics 520 accordingly to zoom in on the focus point. Where appropriate, the positioning system (if the imaging system 500 is mounted on a positioning system) automatically repositions the imaging system 500 as needed to center the zoomed in view on the focus point.

Still referring to FIG. 6, in some examples, the imaging system 500 automatically changes between different autofocus modes. For example, if the current FoV does not include any focus point defined by a medical instrument, the controller 530 may perform autofocus based on a preset criteria, e.g., to obtain the sharpest image or to focus on the center of the FoV. When a focus point defined by a medical instrument is brought into the FoV, the controller 530 may automatically switch mode to autofocus on the focus point. In some examples, the imaging system 500 changes between different autofocus modes in response to user input, e.g., in response to user command via a user interface, voice input, or activation of a foot pedal. In various examples of autofocusing, whether or not relative to a medical instrument, the imaging system 500 is configured to maintain the focus as the zoom is adjusted.

Still referring to FIG. 6, in some examples, the imaging system 500 generates a depth map (not shown). This is performed by capturing images of the same FoV, wherein the imaging system 500 focuses on points at a plurality of depths, e.g., different depths, to simulate 3D depth perception. For example, the imaging system 500 performs autofocusing through a predefined depth range, e.g., through a depth of approximately 1 cm, and capturing focused images at a plurality of distinct or different depths, e.g., at increments of approximately 1 mm, through a depth range, e.g., the predefined depth range. The plurality of images captured at the corresponding plurality of different depths is transmitted to an external system, e.g., an image viewing workstation, wherein the plurality of images is aggregated into a set of depth images to form a depth map for the same FoV. The depth map provides focused views of the FoV, at different depths, and comprises contours, color-coding, and/or other indicators of different depths. The external system (not shown) provides a user interface (not shown) that allows a user to navigate through the depth map.

Still referring to FIG. 6, in some examples, the optical imaging system 500 could be configured with a relatively large DoF. The 3D scanner 545 is used to create a depth map of the viewed area; and the depth map is registered to the image captured by the camera 535. Image processing is performed, e.g., using the controller 530 or an external processor, to generate a pseudo 3D image, for example by visually encoding, e.g., using color, artificial blurring, or other visual symbols, different parts of the captured image according to the depth information from the 3D scanner 545.

Figure 7:
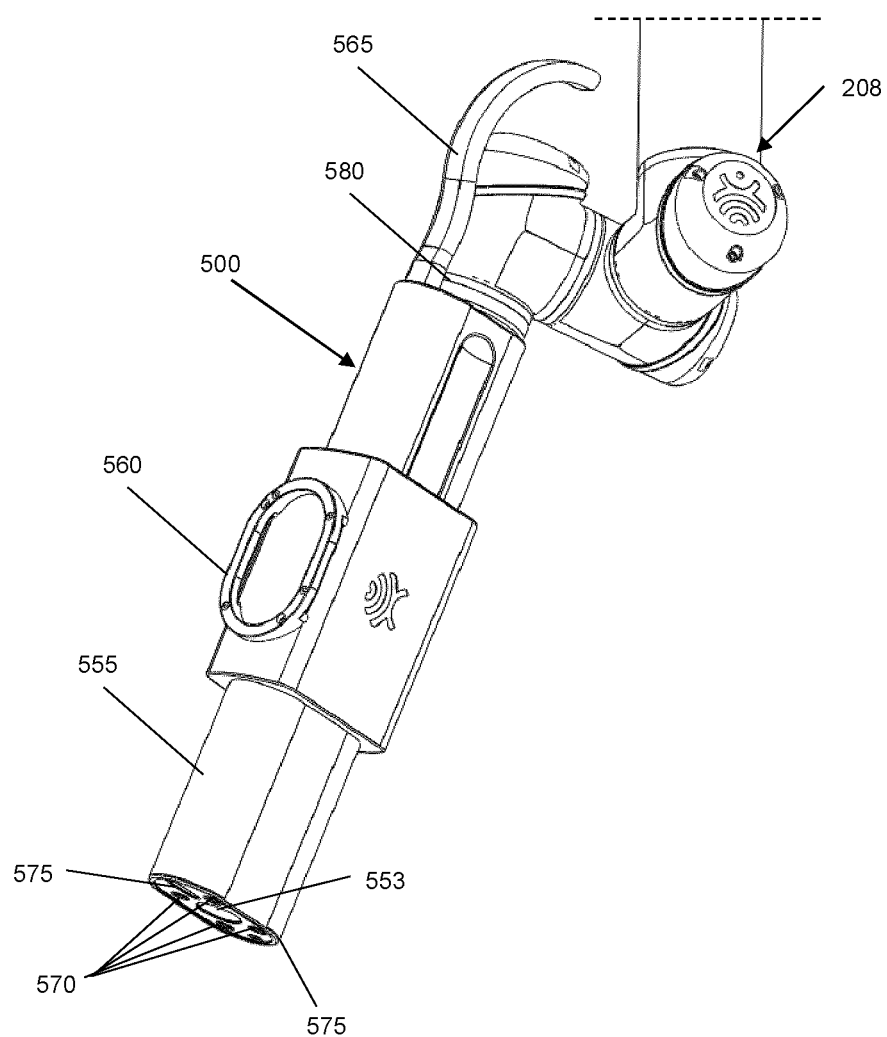
FIG. 7 is a diagram illustrating a perspective view of an example optical imaging system, in accordance with an embodiment of the present disclosure.
Figure 8:
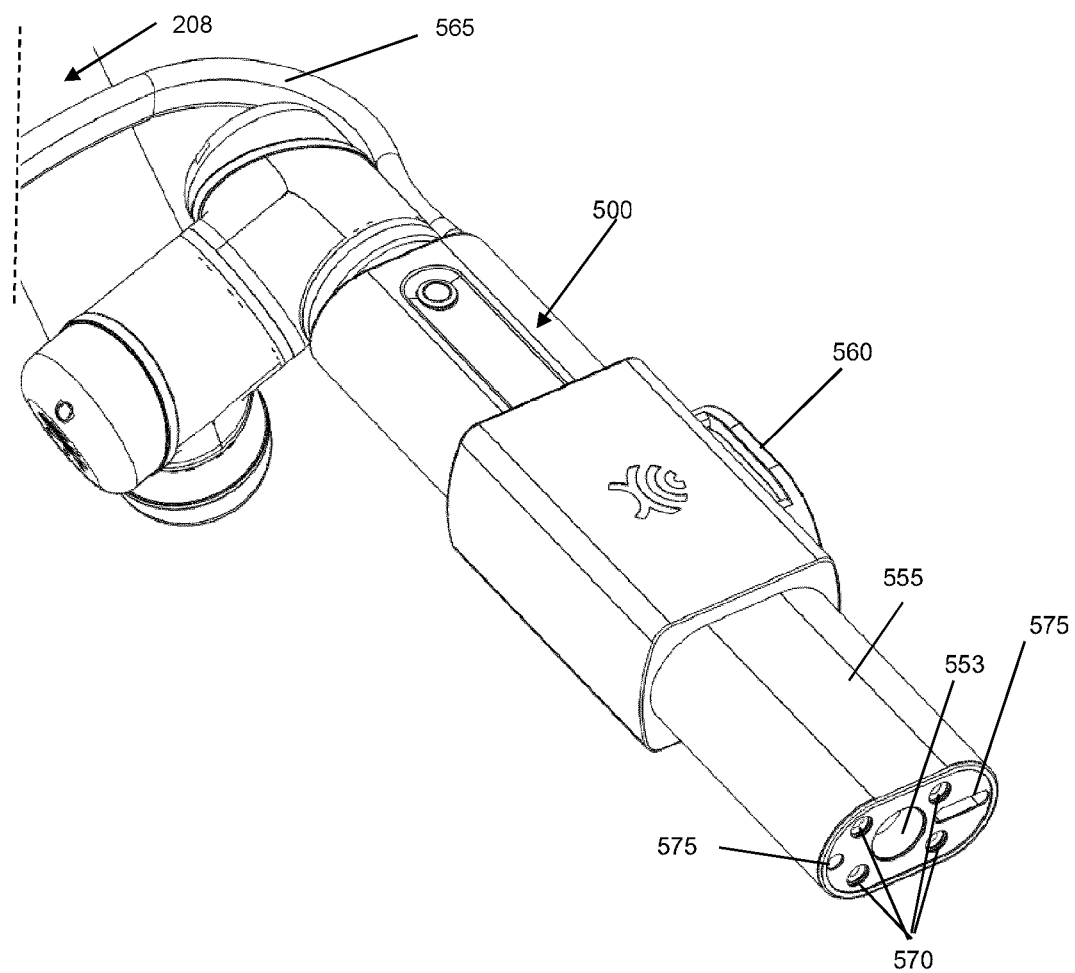
FIG. 8 is a diagram illustrating an alternate perspective view of the example optical imaging system, as shown in FIG. 7, in accordance with an embodiment of the present disclosure.

Referring to FIGS. 7 and 8, together, these diagrams illustrate, in alternate perspective views, an example embodiment of the imaging system 500, in accordance with an embodiment of the present disclosure. In this example, the imaging system 500 is shown mounted to the positioning system 208, e.g., a robotic arm, of a navigation system. The imaging system 500 is shown with a housing 555 that encloses the zoom and focus optics, the zoom and focus actuators, the camera, the controller, and the 3D scanner. The housing is provided with a frame 560 on which trackable markers are mounted to enable tracking by the navigation system. The imaging system 500 communicates with the navigation system via a cable 565 (cutaway view in FIG. 8). The distal end of the imaging system 500 is provided with light sources 570. The example shows four broad spectrum LEDs; however, more or less light sources can be used, of any suitable type. Although the light sources 570 are shown provided surrounding the aperture 553 of the imaging system 500, in other examples, the light source(s) 570 is located elsewhere on the imaging system 500. The distal end of the imaging system 500 further has openings 575 for the cameras of the integrated 3D scanner. A support connector 580 for mounting the imaging system 500 to the positioning system 208 is also shown, as well as the frame 560 for mounting trackable markers.

Figure 9:
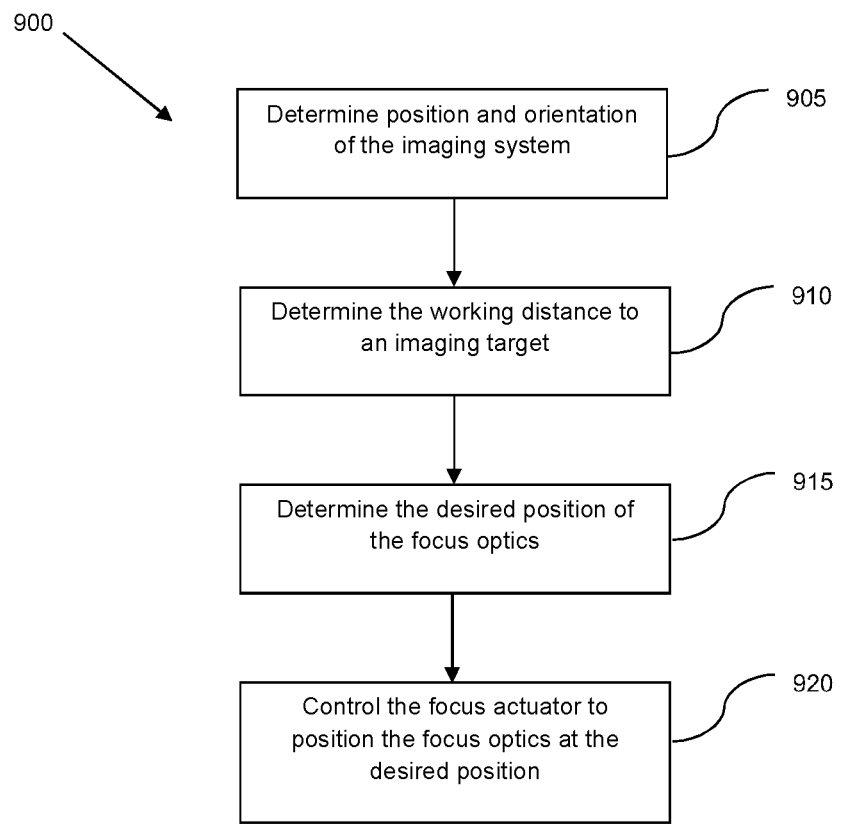
FIG. 9 is a flow diagram illustrating an example method of autofocusing using an example optical imaging system, in accordance with an embodiment of the present disclosure.

Referring to FIG. 9, this flow diagram illustrates an example method 900 of autofocusing during a medical procedure, in accordance with an embodiment of the present disclosure. The example method 900 is performed by way of an example optical imaging system, as disclosed herein. The method 900 comprises: determining the position and orientation of the imaging system, as indicated by block 905, wherein determining the position and orientation of the imaging system comprises is performed by tracking the imaging system, by performing calibration, or by tracking the positioning system on which the imaging system is mounted, for example; determining the WD between the imaging system and the imaging target, as indicated by block 910, e.g., wherein determining the position of the imaging target is performed by a navigation system, and wherein information relating to the position of the imaging target is used together with the position and orientation information of the imaging system to determine the WD; determining the desired position of the focus optics in order to achieve a focused image, as indicated by block 915; and controlling the focus actuator, e.g., by a controller of the imaging system, to position the focus optics at the desired position, as indicated by block 920, whereby a focused image is capturable, for example, by using a camera of the optical imaging system.

Figure 10:
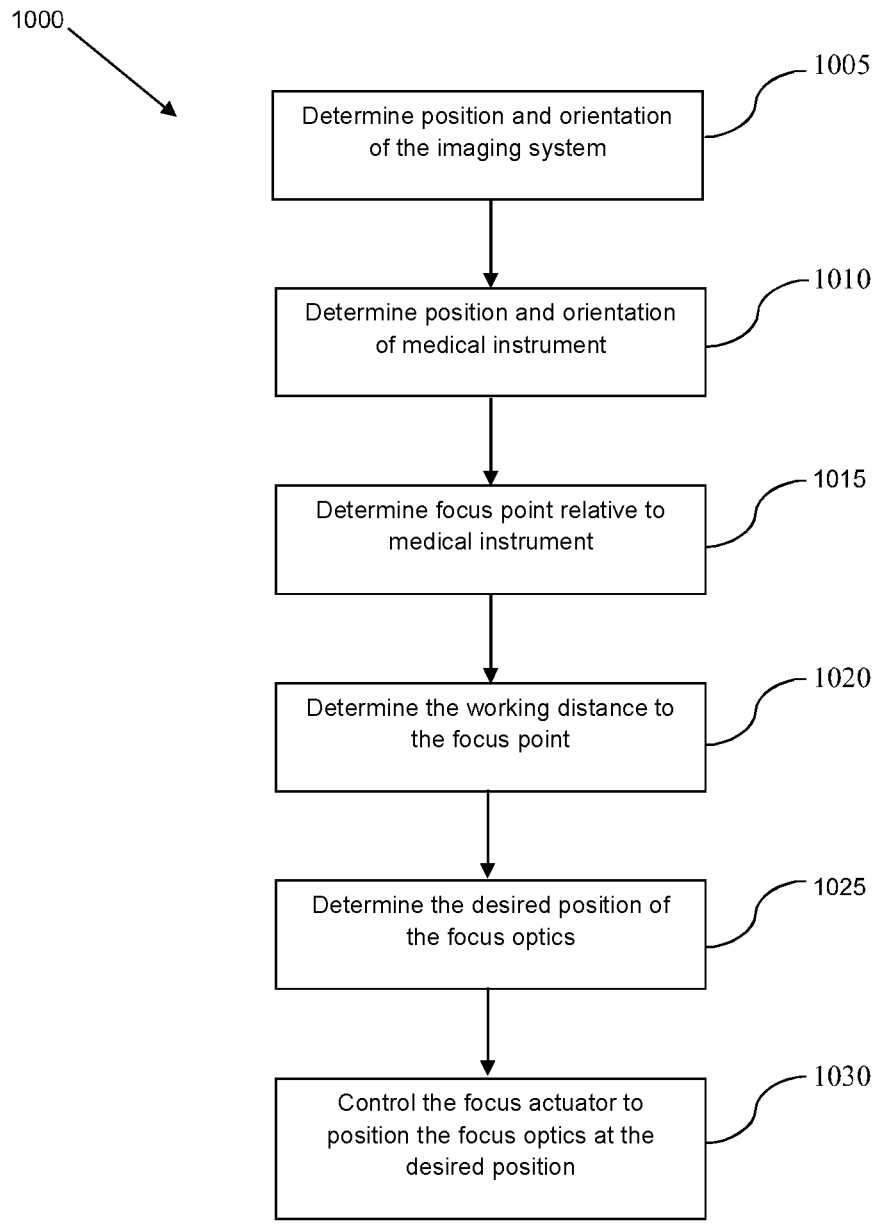
FIG. 10 is a flow diagram illustrating an example method of autofocusing relative to a medical instrument, using an example optical imaging system, in accordance with an embodiment of the present disclosure.

Referring to FIG. 10, this flow diagram illustrates an example method 1000 of autofocusing relative to a medical instrument during a medical procedure, in accordance with an embodiment of the present disclosure. The example method 1000 is performable using an example optical imaging system as disclosed herein. The example method 1000 is similar to the example method 900. The example method 1000 comprises: determining the position and orientation of the imaging system, as indicated by block 1005, wherein determining the position and orientation of the imaging system is performable by tracking the imaging system, by performing calibration, or by tracking the positioning system on which the imaging system is mounted, for example; determining the position and orientation of the medical instrument, as indicated by block 1010, wherein determining the position and orientation of the medical instrument is performed by tracking the medical instrument, e.g., using a navigation system, by sensing the medical instrument, e.g., using an infrared or machine vision component of the imaging system, or by any other suitable techniques; determining the focus point relative to the medical instrument, as indicated by block 1015, wherein determining the focus point comprises looking-up preset definitions, e.g., stored in a database, of focus points for different medical instruments, and calculating the focus point for the particular medical instrument being used; determining the WD between the imaging system and the focus point, as indicated by block 1020; determining the desired position of the focus optics in order to achieve a focused image, as indicated by block 1025; controlling the focus actuator, e.g., by a controller of the imaging system, to position the focus optics at the desired position, as indicated by block 1030, whereby a focused image is capturable, for example, using a camera of the optical imaging system.

Referring to FIG. 11, this set of diagrams illustrate, in perspective views, some examples of the imaging system 500 configured to perform autofocusing relative to an instrument using in the medical procedure, in accordance with an embodiment of the present disclosure. For example, the position and orientation of a medical instrument, such as a tracked pointer tool 222, is determined; and the controller 530 performs autofocusing to focus the captured image on a point defined relative to the medical instrument. In the examples shown in FIG. 11, the tracked pointer tool 222 has a defined focus point at the distal tip of the pointer 222. As the tracked pointer tool 222 is moved, the WD between the optical imaging system 500 and the defined focus point (at the distal tip of the tracked pointer tool 222) changes (from D1 in the left image to D2 in the right image, for example). The autofocusing is performed in a manner similar to that as above described; however, instead of autofocusing on a viewing target in the surgical field, the imaging system 500 focuses on a focus point that is defined relative to the medical instrument. The medical instrument is used in the surgical field to guide the imaging system 500 to autofocus on different points in the surgical field, as below discussed, thereby enabling a surgeon to change the focus within a FoV, e.g., focus on a point other than at the center of the FoV, without changing the FoV, and without needing to manually adjust the focus of the imaging system 500. Where the FoV includes objects at different depths, the surgeon uses the medical instrument, e.g., a pointer, to indicate to the imaging system 500 the object and/or depth desired for autofocusing.

Referring back to FIG. 1 to FIG. 11, the example methods 900, 1000 described above are entirely performable by the controller of the imaging system, or are partly performed by the controller and partly performed by an external system. For example, one or more of: determining the position/orientation of the imaging system, determining the position/orientation of the imaging target or medical instrument, determining the WD, or determining the desired position of the focus optics is performed by one or more external systems. The controller of the imaging system may simply receive commands, from the external system(s) to position the focus optics at the desired position, or the controller of the imaging system may determine the desired position of the focus optics after receiving the calculated WD from the external system(s).

Figure 12A:
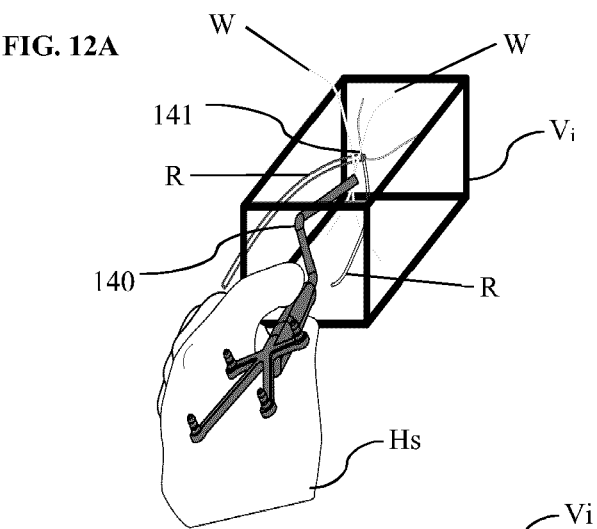
FIG. 12A is a diagram illustrating a perspective view of a 3D navigation system, in operation, in accordance with an embodiment of the present disclosure.
Figure 12B:
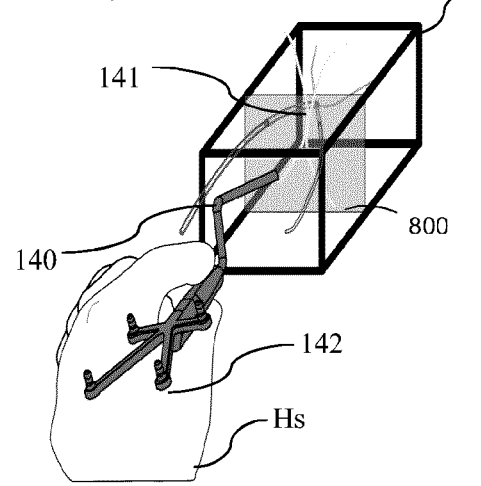
FIG. 12B is a diagram illustrating a perspective view of a 3D navigation system, in operation, as shown in FIG. 12A, in accordance with an embodiment of the present disclosure.
Figure 12C:
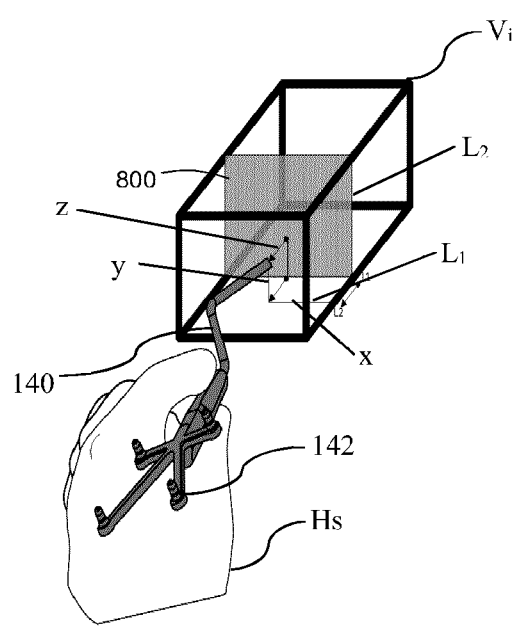
FIG. 12C is a diagram illustrating a perspective view of a 3D navigation system, in operation, as shown in FIG. 12B, in accordance with an embodiment of the present disclosure.

Referring to FIG. 12A to FIG. 12C, together, these diagrams illustrate, in perspective views, a surgeon hand $H_s$ operating a 3D navigation system 1200 in relation to an interrogation volume $V_i$, comprising at least one proprioception feature, in accordance with some embodiments of the present disclosure. The at least one proprioception feature comprises at least one communication feature for providing 3D (depth information) to the surgeon. The at least one communication feature comprises at least one of at least one active tool 140, such as a tracked tool, above-discussed, at least one camera (not shown), and software (not shown) for generating a 3D perception, e.g., by providing a combination of perceivable signals, the perceivable signals relating to at least one sense, such as touch (haptic feedback), e.g., a vibration, vision (visual cues), e.g., light indicators, and sound (audio cues), e.g., a beeping sound. The perceivable signal combination comprises at least two perceivable signals, e.g., providing a plurality of sensory inputs in combination with 3D feedback (beyond the visual cues), readily perceivable by a surgeon.

Still referring to FIG. 12A to FIG. 12C, for example, the systems and methods use audiohaptics, visualacoustic, or any combination of visual, haptic, and acoustic feedback, signals, or cues to provide a surgeon with a depth indication in relation to each 2D view of a scene, e.g., in an interrogation volume. In another example, the systems and methods use an acoustic feedback comprises a periodic beep along a distance from a given surface, wherein the periodic beep comprises a reducing period as a function of the tool, e.g., the active tool 140, traveling from the given surface 800 to a patient, an anatomical target 141, or a tissue intended for resection (not shown), and wherein the period approaches zero at a point where the tool, e.g., the active tool 140, touches the patient, e.g., at the given surface 800, the anatomical target 141, or the tissue intended for resection (not shown). Thus, the 3D navigation system 1200 of the present disclosure is configured to provide depth information to a surgeon in the absence of stereo imaging.

Referring to FIG. 12A, for example, this diagram illustrates a perspective view of a surgeon hand $H_s$ operating a 3D navigation system 1200 in relation to an interrogation volume $V_i$, comprising at least one proprioception feature, in accordance with some embodiments of the present disclosure. A surgeon working in a surgical field or an interrogation volume $V_i$, containing "white" matter W and vasculature R of the patient. Noted is that the "black box" or the interrogation volume $V_i$ may represent a port, a portion of the patient anatomy, or other structure defining or containing internal anatomical or resectable parts. Using a tracked pointer tool 142, the surgeon defines a plane within the interrogation volume $V_i$, the reference frame, or the interrogation volume $V_i$ by indicating either a point or a number of points on the anatomical parts or other structure intended for use as "landmarks" or "barriers" to facilitate accurately determining positions thereof. In the 3D navigation system 1200, tracking of the tracked tool 140, e.g., via the tracked pointer tool 142, is performable by at least one technique, such as sonar tracking, ultrasonic tracking, and optical tracking.

Referring to FIG. 12B, for example, this diagram illustrates a perspective view of a surgeon hand $H_s$ operating a 3D navigation system 1200 in relation to an interrogation volume $V_i$, comprising at least one proprioception feature, in accordance with some embodiments of the present disclosure. The surgeon defines a plane, such as the reference plane 800, in accordance with an embodiment of the present disclosure. The reference plane 800 defines a "zero" point by which location or depth of landmarks, barriers, or targets and their relative positions are determinable. In addition, in some embodiments, either a reference plane or a reference volume is definable, e.g., wherein frequency is 3D location-dependent.

Referring to FIG. 12C, for example, this diagram illustrates a perspective view of a surgeon hand $H_s$ operating a 3D navigation system 1200 in relation to an interrogation volume $V_i$, comprising at least one proprioception feature, in accordance with some embodiments of the present disclosure. For example, the 3D navigation system 1200 comprises at least one communication feature, such as an audio sensory device and a visual sensory device, for providing 3D (including depth information) to the surgeon. In this example, the surgeon has a 2D view of the surgical field of interest, but the surgeon also has a depth cue provided by a periodic or persistent beep indicating a position P of the tracked pointer tool 142 relative to an intraoperatively defined plane, such as a the reference plane 800, wherein the position P is defined by coordinates x, y, and z as related to both the reference plane 800 and the boundaries of the interrogation volume $V_i$.

Still referring to FIG. 12C (anatomy removed for illustrative purposes only) in relation to FIG. 12A, when the active tool 140 arrives at the reference plane 800 at a location L1, the audio sensory device (not shown) emits a sound, such as an audible cue, e.g., a constant beep (as the periodic beep then has a period=0). However, when the surgeon moves the active tool 140 to another plane at a location L2, the audio sensory device emits a sound, such as an audible cue, e.g., a periodic beep (as the periodic beep then has a period>0). The period increases, thereby producing an incremental beeping sound, and thereby facilitating gauging a distance in relation to the plane having the location L1.

Referring back to FIGS. 12A to 12C, an example of the 3D navigation system 1400 in operation is illustrated. However, a plethora of other operational applications are encompassed by the present disclosure. For example, in other embodiments of the present disclosure, the 3D navigation system 1200 comprises a dull pressure spring (not shown) for indicating a distance from the reference plane 800 at a location L1 based on a pressure experienced by the spring. Alternatively, in another embodiment, the active tool 140 is embeddable with an arrangement of strip light-emitting diode (LED), e.g., lengthwise embeddable, the arrangement, e.g., of activated LEDs, configured to shorten and lengthen based on the distance from the reference plane 800 at a location L1. In yet another embodiment, the location L1 of the reference plane 800 is importable into the 3D navigation system 1200, e.g., via a user interface (UI) (not shown) for further assisting the surgeon.

Referring to FIG. 13, this diagram illustrates, in a perspective view, an optical imaging system 500' using a 3D navigation system 1200, capable of enhanced autofocusing relative to a medical instrument, e.g., a tracked pointer tool 222, in accordance with an alternative embodiment of the present disclosure. The imaging system 500' is configured to perform enhanced autofocusing relative to an instrument, e.g., a tracked pointer tool 222, using in the medical procedure, by example only. For example, the position and orientation of a medical instrument, such as a tracked pointer tool 222, is determined; and the controller 530 performs enhanced autofocusing to focus the captured image on a point defined relative to the medical instrument. The optical imaging system 500' comprises an optical imaging assembly and at least one detector operable with the optical imaging assembly 500'. The at least one detector of the optical imaging assembly comprises at least one of a single camera system and a dual camera system (not shown).

Still referring to FIG. 13, the tracked pointer tool 222 has a defined focus point at the distal tip of the tracked pointer tool 222. As the tracked pointer tool 222 is moved, the WD between the optical imaging system 500 and the defined focus point (at the distal tip of the tracked pointer tool 222) changes (from D1 in the left image to D2 in the right image, for example). The enhanced autofocusing is performed in a manner similar to that, as above described; however, instead of autofocusing on a viewing target in the surgical field, the optical imaging system 500' focuses on a focus point that is defined relative to the medical instrument.

Still referring to FIG. 13, the medical instrument is used in the surgical field to guide the optical imaging system 500' to autofocus on different points in the surgical field, as below discussed, thereby enabling a surgeon to change the focus within a FoV, e.g., focus on a point other than at the center of the FoV, without changing the FoV, and without needing to manually adjust the focus of the optical imaging system 500'. Where the FoV includes objects at different depths, the surgeon uses the medical instrument, e.g., a pointer, to indicate to the optical imaging system 500' the object and/or depth desired for enhanced autofocusing.

Still referring to FIG. 13, the optical imaging system 500' is configured to use a method of enhanced autofocusing, e.g., by way of the 3D navigation system 1200. The optical imaging system 500' comprises at least one of: (a) a single array of detectors, such as a plurality of video cameras, (b) a pair of detectors, such as in a video loop configuration and a pair of video cameras, (c) a pair of detectors capable of stereovision, (d) two detectors, wherein each detector comprises at least one of a distinct resolution and a distinct color, and whereby differentiation between each view of a stereoscopic view is enabled, (e) a device configured to render an image on a display, for updating the image on the display, and for tracking a tip of a tool, (f) a sensory device configured to detect a plurality of sensory input signals, analyze the plurality of sensory input signals, translate or transform the plurality of sensory input signals into a plurality of sensory output signals, and transmit the plurality of sensory output signals, wherein the plurality of sensory output signals comprises at least two of a visual feedback, a haptic feedback, and an audio feedback, and (g) at least one ultra-high-definition (UHD) detector, such as at least one UHD camera disposed in relation to a distal end of a robotic arm, with a thin focus frame for facilitating movement of a focal plane by way of moving a tool, such as the tracked pointer tool 222, whereby 3D image enhanceable.

Still referring to FIG. 13, if the optical imaging system 500' comprises two detectors for achieving a stereoscopic view, e.g., an inferring view using two detectors, 3D navigation is achievable, e.g., via virtual 3D navigation, wherein a tool tip is viewable relative to an image rendered on a display, wherein the plurality of sensory output signals comprises a visual feedback and a haptic feedback, wherein the haptic feedback provides a sense of feel, whereby the sense of feel provide a surgeon with a sense of three-dimensionality. The sensory device comprises four sensors, for example, to enhance the haptic feedback provided to the surgeon. The tool itself is "active" wherein the plurality of sensory output signals may emanate from the tool itself. The active tool itself, thus, comprises the sensory device. The sensory device further comprises at least one visual indicator, such as at least one light indicator, the at least one visual indicator activable when the tool approaches a target or a barrier, e.g., in response to sending proximity thereto.

Still referring to FIG. 13, the haptic feedback comprises a vibration, for example, emanating from the tool, itself, whereby the sense of feel is immediate. At least one of the visual feedback, the audio feedback, and the haptic feedback further comprises at least one of variable amplitude and variable frequency for providing the surgeon with an indication as to an appropriate degree of contact with the tissue. The optical imaging system 500', using the 3D navigation system 1200, utilizes tools and sensors, such as two detectors disposed in relation to a device positioning system (DPS), e.g., a drive system comprising a robotic arm, for providing and enhancing 3D navigation. The optical imaging system 500', using the 3D navigation system 1200, integrates the foregoing features.

Referring back to FIGS. 12A to 13, a 3D navigation system 1200 for enhancing feedback during a medical procedure comprises: an optical imaging system comprising: an optical assembly comprising movable zoom optics and movable focus optics; a zoom actuator for positioning the zoom optics; a focus actuator for positioning the focus optics; a controller for controlling the zoom actuator and the focus actuator in response to received control input; at least one detector for capturing an image of at least one of a target and an obstacle, the at least one detector operable with the optical assembly; and a proprioception feature operable with the optical imaging system for generating a 3D perception, the proprioception feature comprising a communication feature for providing 3D information, the 3D information comprising real-time depth information in relation to real-time information, such as real-time planar information and real-time volumetric information, in relation to an interrogation volume, the zoom optics and the focus optics independently movable by the controller by way of the zoom actuator and the focus actuator, respectively, and the optical imaging system configured to operate at a minimum WD from at least one of the target and the obstacle, the WD defined between an aperture of the optical assembly and at least one of the target and the obstacle, whereby feedback during the medical procedure is enhanceable, in accordance with an embodiment of the present disclosure. By enhancing feedback during the medical procedure, a surgeon's "feel" during the medical procedure is maximized, a surgeon's fatigue is minimized, a patient's tissue trauma is minimized and medical or surgical error is minimized. In the embodiments of the present disclosure, the three-dimensional feedback (e.g., touch, sight, and sound feedback) is used in conjunction with sensed information as a function of the three-dimensional spatial coordinates (e.g., x, y, and z coordinates).

Figure 14:
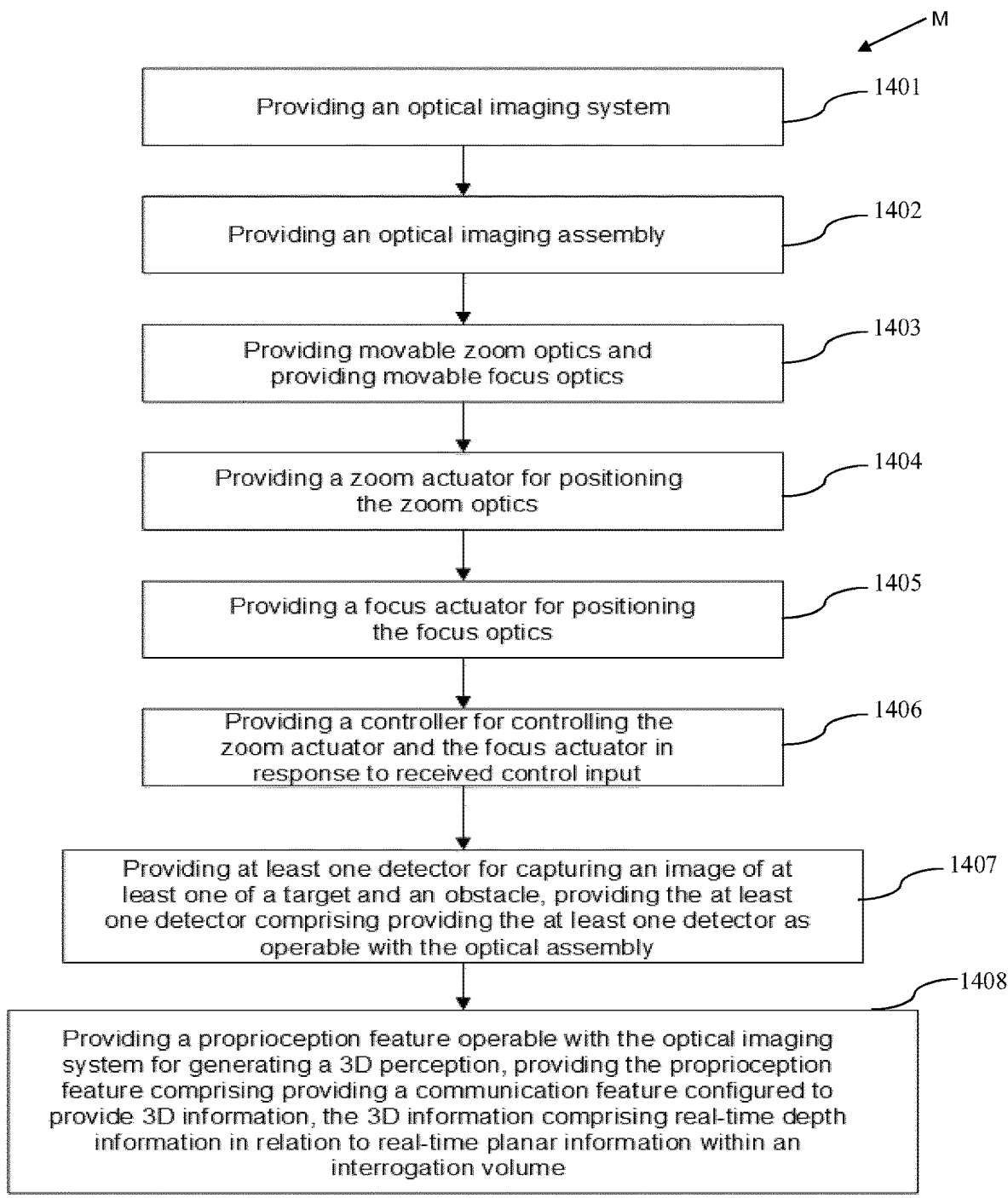
FIG. 14 is a flow diagram illustrating a method of fabricating a 3D navigation system, in accordance with an embodiment of the present disclosure.

Referring to FIG. 14, this flow diagram illustrates a method M1 of fabricating a 3D navigation system 1200 system for enhancing feedback during a medical procedure, in accordance with an embodiment of the present disclosure. The M1 comprises: providing an optical imaging system, as indicated by block 1401, providing the optical imaging system comprising: providing an optical assembly, as indicated by block 1402, providing the optical assembly comprising providing movable zoom optics and providing movable focus optics, as indicated by block 1403; providing a zoom actuator for positioning the zoom optics, as indicated by block 1404; providing a focus actuator for positioning the focus optics, as indicated by block 1405; providing a controller for controlling the zoom actuator and the focus actuator in response to received control input, as indicated by block 1406; providing at least one detector for capturing an image of at least one of a target and an obstacle, providing the at least one detector comprising providing the at least one detector as operable with the optical assembly, as indicated by block 1407; and providing a proprioception feature operable with the optical imaging system for generating a 3D perception, providing the proprioception feature comprising providing a communication feature configured to provide 3D information, the 3D information comprising real-time depth information in relation to real-time planar information in relation to an interrogation volume, as indicated by block 1408, providing the zoom optics and providing the focus optics comprising providing the zoom optics and providing the focus optics as independently movable by the controller by way of the zoom actuator and the focus actuator, respectively, and providing the optical imaging system comprising configuring the optical imaging system to operate at a minimum WD from at least one of the target and the obstacle, the WD defined between an aperture of the optical assembly and at least one of the target and the obstacle, whereby feedback during the medical procedure is enhanceable.

Figure 15:
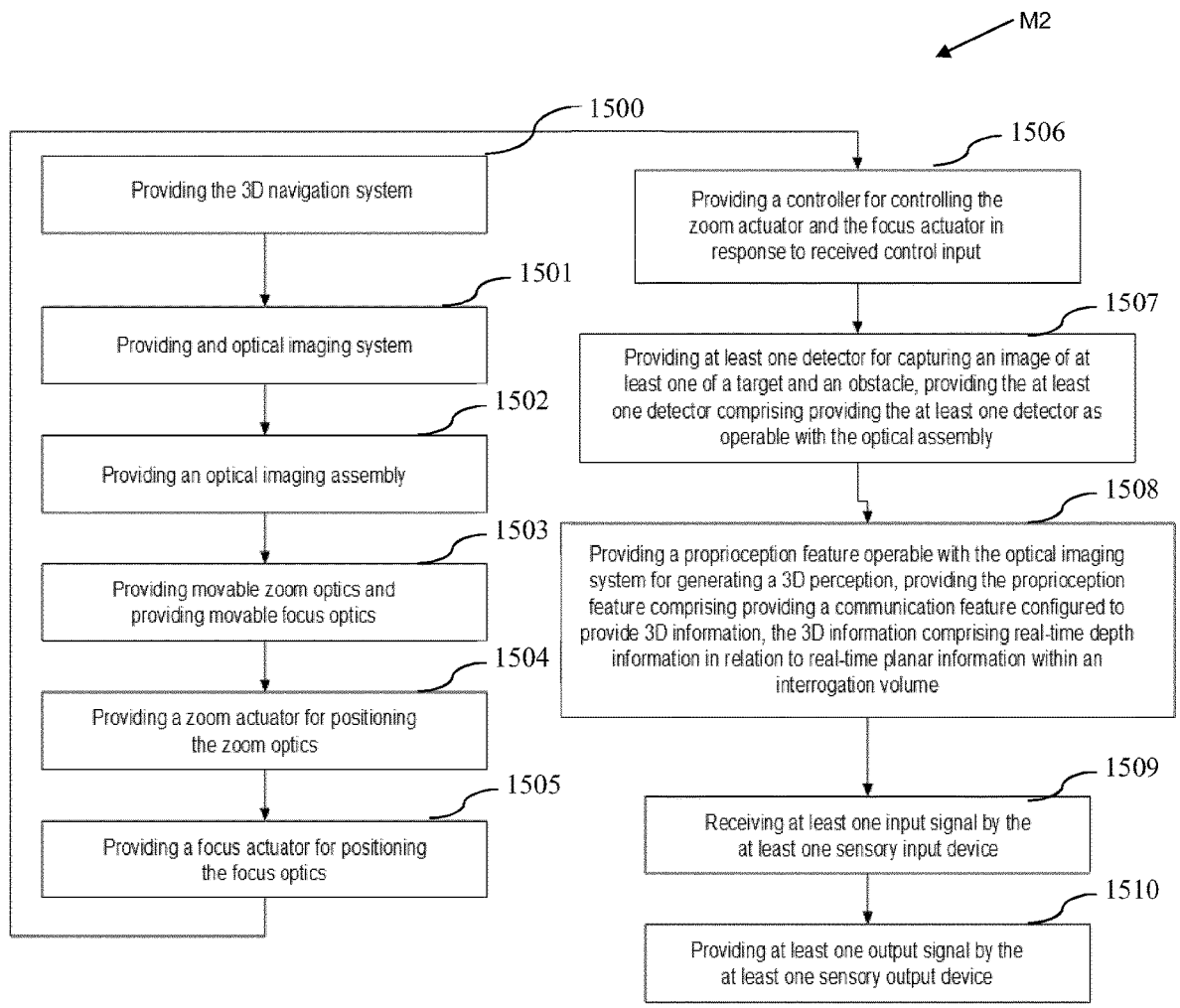
FIG. 15 is a flow diagram illustrating a method of enhancing surgical navigation by way of a 3D navigation system, in accordance with an embodiment of the present disclosure.

Referring to FIG. 15, this flow diagram illustrates a method M2 of enhancing feedback during a medical procedure by way of a 3D navigation system 1200, in accordance with an embodiment of the present disclosure. The method M2 comprises: providing the 3D navigation system, as indicated by block 1500, providing the 3D navigation system comprising: providing an optical imaging system, as indicated by block 1501, providing the optical imaging system comprising: providing an optical assembly, as indicated by block 1502, providing the optical assembly comprising providing movable zoom optics and providing movable focus optics, as indicated by block 1503; providing a zoom actuator for positioning the zoom optics, as indicated by block 1504; providing a focus actuator for positioning the focus optics, as indicated by block 1505; providing a controller for controlling the zoom actuator and the focus actuator in response to received control input, as indicated by block 1506; providing at least one detector for capturing an image of at least one of a target and an obstacle, providing the at least one detector comprising providing the at least one detector as operable with the optical assembly, as indicated by block 1507; and providing a proprioception feature operable with the optical imaging system for generating a 3D perception, providing the proprioception feature comprising providing a communication feature for providing 3D information, the 3D information comprising real-time depth information in relation to real-time planar information in relation to an interrogation volume, providing the communication feature comprises providing at least one sensory input device and providing at least one sensory output device, and providing the communication feature comprises providing the communication feature as operable by way of a set of executable instructions storable on a nontransitory memory device, as indicated by block 1508, providing the zoom optics and providing the focus optics comprising providing the zoom optics and providing the focus optics as independently movable by the controller by way of the zoom actuator and the focus actuator, respectively, and providing the optical imaging system comprising configuring the optical imaging system to operate at a minimum WD from at least one of the target and the obstacle, the WD defined between an aperture of the optical assembly and at least one of the target and the obstacle; receiving at least one input signal by the at least one sensory input device, as indicated by block 1509; and providing at least one output signal by the at least one sensory output device, as indicated by block 1510, thereby enhancing feedback during the surgical procedure.

While some embodiments or aspects of the present disclosure is implemented in fully functioning computers and computer systems, other embodiments or aspects is capable of being distributed as a computing product in a variety of forms and is capable of being applied regardless of the particular type of machine or computer readable media used to actually effect the distribution.

At least some aspects disclosed are embodied, at least in part, in software. That is, some disclosed techniques and methods is carried out in a computer system or other data processing system in response to its processor, such as a microprocessor, executing sequences of instructions contained in a memory, such as ROM, volatile RAM, non-volatile memory, cache or a remote storage device.

A computer readable storage medium is used to store software and data which when executed by a data processing system causes the system to perform various methods or techniques of the present disclosure. The executable software and data is stored in various places including for example ROM, volatile RAM, non-volatile memory and/or cache. Portions of this software and/or data are stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium is the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium is provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein are implemented by software, or a combination of software and hardware. Elements of the system that are implemented via software are written in a high-level procedural language such as object oriented programming or a scripting language. Accordingly, the program code is written in C, C++, J++, or any other suitable programming language and may comprise modules or classes, as is known to those skilled in object oriented programming. At least some of the elements of the system that are implemented via software are written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps is varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail is made, without departing from the spirit and scope of the present disclosure, as set forth in the appended claims, as is apparent to those of ordinary skill in the art, are also encompassed by the present disclosure.

INDUSTRIAL APPLICABILITY

Generally, the present disclosure industrially applies to optical imaging systems. More particularly, the present disclosure industrially applies to optical imaging systems for use in image guided medical procedures. Even more particularly, the present disclosure industrially applies to optical imaging systems for use in image guided medical procedures involving a pointer tool.

What is claimed:

1. A 3D navigation system for enhancing feedback during a medical procedure, the system comprising:
   an optical imaging system comprising:
      an optical assembly comprising movable zoom optics and movable focus optics;
      a zoom actuator for positioning the zoom optics;
      a focus actuator for positioning the focus optics;
      a controller for controlling the zoom actuator and the focus actuator in response to received control input;
      at least one detector for capturing an image of at least one of a target and an obstacle, the at least one detector operable with the optical assembly;
   a proprioception feature operable with the optical imaging system for generating and enhancing a 3D perception, the proprioception feature comprising a communication feature for providing 3D information, the communication feature comprising a tracked tool and a capture feature, the capture feature comprising a 3D infrared (IR) optical tracking stereo camera, the 3D information comprising real-time depth information in relation to real-time planar information in relation to an interrogation volume, the capture feature configured to acquire 3D image data by inwardly precessing in a spiral pattern and outwardly precessing in the spiral pattern within an interrogation volume, whereby acquired 3D image data is provided, and the capture feature having a sensory device for translating the acquired 3D image data into a usable form, whereby translated acquired image data is provided; and a display device for presenting the 3D information, based on the translated acquired 3D image data, the 3D information applicable to a particular context of use, the zoom optics and the focus optics respectively independently movable by the controller by way of the zoom actuator and the focus actuator, respectively, and the optical imaging system configured to operate at a minimum working distance from at least one of the target and the obstacle, the working distance defined between an aperture of the optical assembly and at least one of the target and the obstacle, whereby feedback during the medical procedure is enhanceable.

2. The system of claim 1, wherein the capture feature further comprises at least one of a vision feature, a sound feature, and a haptic feature, each of the vision feature, the sound feature, and the haptic feature respectively configured to acquire visual data, audio data, and haptic data, wherein the communication feature further comprises software for generating the 3D perception by providing a combination of perceivable signals, the combination of perceivable signals relating to at least two of a visual cue based on the visual data, an audio cue based on the audio data, and a haptic feedback based on the haptic data, whereby a plurality of sensory inputs in combination with 3D feedback is provided, wherein the capture feature further comprises an electromagnetic system configured to use at least one receiver coil disposed in relation to the tracked tool, the electromagnetic system comprising a field transmitter, wherein the vision feature comprises a shadowing feature, wherein the particular context of use comprises at least one of a medical context and a surgical context, wherein the proprioception feature and the vision feature, together, optimize the 3D perception in relation to an interrogation volume by at least one of:

implementing focused visual targets by maintaining at least one of a focal plane and a focal point, using visual obscuration throughout the interrogation volume, and using a focused target in the depth dimension;

implementing serial focus adjustments by performing dynamic adjustment of a focal distance to create multiple focal points across a range of the interrogation volume; and implementing an immersive contextual volume of view by generating a volume of view in simultaneous focus, whereby continuous contextual information throughout the interrogation volume is provided, wherein the communication feature comprises at least one sensory input device and at least one sensory output device, and wherein the communication feature is operable by way of a set of executable instructions storable on a nontransitory memory device.

3. The system of claim 2, wherein the at least one sensory input device comprises at least one of the at least one detector and an active tool, and wherein the at least one sensory input device is configured to receive an input signal from at least one of a visual input, an audio input, and a haptic input.

4. The system of claim 3, wherein the visual input comprises at least one of an image obtained by the at least one detector, wherein the audio input comprises at least one of voice-recognized observations, and wherein the haptic input comprises at least one of pressure exerted by tissue on a dull pressure spring.

5. The system of claim 2, wherein the at least one sensory output device comprises at least one of a display device and an active tool, and wherein the at least one sensory output device is configured to transmit an output signal in the form of at least one of a visual output, an audio output, and a haptic output.

6. The system of claim 5, wherein the visual output comprises at least one of a visual cue, wherein the audio output comprises at least one of an audio cue, and wherein the haptic output comprises at least one of a touch cue.

7. The system of claim 6, wherein the visual cue comprises a light indication, wherein the audio cue comprises a beep indication, and wherein the touch cue comprises a vibratory indication.

8. The system of claim 7, wherein a reference plane is definable in relation to the interrogation volume by at least one point corresponding to at least one of a landmark and a barrier for facilitating respectively determining a position of at least one of the target and the obstacle, wherein the at least one point is definable by a tracked pointer tool, and wherein the tracked pointer tool is trackable by at least one technique of sonar tracking, ultrasonic tracking, and optical tracking.

9. The system of claim 8, wherein the beep indication comprises a range from a periodic beep to a persistent beep, the beep indication indicating a position of a tracked pointer tool relative to the reference plane, and wherein the position of the tracked pointer tool is defined by coordinates x, y, and z in relation to both the reference plane and at least one boundary plane of the interrogation volume, and whereby gauging a distance to at least one of the target and the obstacle is facilitated.

10. The system of claim 8, further comprising an active tool having an active tool tip, the active tool comprising at least one of a linear arrangement of light-emitting diodes, at least a portion of the light-emitting diodes activated as a function of a distance of the active tool tip from the reference plane having a first location, wherein the active tool is configured to relocate a focal plane, and wherein the first location of the reference plane is importable via a user interface for further enhancing 3D navigation.

11. The system of claim 5, wherein the output signal comprises at least one of a variable amplitude and a variable frequency, and wherein at least one of the variable amplitude and the variable frequency is variable as a function of proximity of the active tool in relation to at least one of the target and the obstacle.

12. The system of claim 11, wherein at least one of the variable amplitude and the variable frequency increases as the active tool moves toward at least one of the target and the obstacle, and wherein at least one of the variable amplitude and the variable frequency decreases as the active tool moves away from at least one of the target and the obstacle.

13. The system of claim 5,
wherein the output signal comprises a signal associated with a trajectory toward the target and a signal associated with a trajectory toward an obstacle, and
wherein the signal associated with a trajectory toward the target and the signal associated with a trajectory toward an obstacle are distinct from one another.

14. The system of claim 2, wherein the communication feature further comprises a device configured to at least one of:
render an image on a display device,
update the image on the display device, and
track a tool tip.

15. The system of claim 2,
wherein the at least one a sensory input device is configured to at least one of: detect a plurality of sensory input signals, analyze the plurality of sensory input signals, at least one of translate and transform the plurality of sensory input signals into a plurality of sensory output signals, and transmit the plurality of sensory output signals,
wherein the plurality of sensory output signals comprises at least two of a visual feedback, a haptic feedback, and an audio feedback.

16. The system of claim 1, wherein the at least one detector comprises at least one of:
a single array of detectors comprising a plurality of video cameras;
a pair of detectors comprising at least one of a video loop configuration and a pair of video cameras;
a pair of detectors capable of stereovision, each detector of the pair of detectors comprising at least one of a distinct resolution and a distinct color, whereby differentiation between each view, corresponding to each detector of the pair of detectors, of a stereoscopic view is enabled,
a stereoscopic microscope apparatus; and
a robotically operated video optical telescopic microscope apparatus.

17. The system of claim 1, wherein the proprioception feature further comprises an ultra-high-definition (HD) thin frame for facilitating movement of a focal plane by way of a tracked pointer tool.

18. A method of fabricating a 3D navigation system for enhancing feedback during a medical procedure, the method comprising:
providing an optical imaging system, providing the optical imaging system comprising:
providing an optical assembly,
providing the optical assembly comprising providing movable zoom optics and providing movable focus optics;
providing a zoom actuator for positioning the zoom optics;
providing a focus actuator for positioning the focus optics;
providing a controller for controlling the zoom actuator and the focus actuator in response to received control input;
providing at least one detector for capturing an image of at least one of a target and an obstacle, providing the at least one detector comprising providing the at least one detector as operable with the optical assembly;
providing a proprioception feature operable with the optical imaging system for generating and enhancing a 3D perception, providing the proprioception feature comprising providing a communication feature configured to provide 3D information, providing the communication feature comprising providing a tracked tool and providing a capture feature, providing the capture feature comprising providing a 3D infrared (IR) optical tracking stereo camera, the 3D information comprising real-time depth information in relation to real-time planar information in relation to an interrogation volume, providing the capture feature comprising configuring the capture feature to acquire 3D image data by inwardly precessing in a spiral pattern and outwardly precessing in the spiral pattern within an interrogation volume, whereby acquired 3D image data is provided, and the providing capture feature comprising providing capture feature with a sensory device for translating the acquired 3D image data into a usable form, whereby translated acquired image data is provided; and
providing a display device for presenting the 3D information, based on the translated data, the 3D information applicable to a particular context of use,
providing the zoom optics and providing the focus optics comprising respectively providing the zoom optics and providing the focus optics as independently movable by the controller by way of the zoom actuator and the focus actuator, respectively,
providing the optical imaging system comprising configuring the optical imaging system to operate at a minimum working distance from at least one of the target and the obstacle, the working distance defined between an aperture of the optical assembly and at least one of the target and the obstacle,
whereby feedback during the medical procedure is enhanceable.

19. The method of claim 18,
wherein providing the capture feature further comprises providing at least one of a vision feature, a sound feature, and a haptic feature, providing each of the vision feature, the sound feature, and the haptic feature respectively comprising configuring each of the vision feature, the sound feature, and the haptic feature to acquire visual data, audio data, and haptic data,
wherein providing the communication feature further comprises providing software for generating the 3D perception by providing a combination of perceivable signals, the combination of perceivable signals relating to at least two of a visual cue based on the visual data, an audio cue based on the audio data, and a haptic feedback based on the haptic data, whereby a plurality of sensory inputs in combination with 3D feedback is provided,
wherein providing the capture feature further comprises providing an electromagnetic system configured to use at least one receiver coil disposed in relation to the tracked tool, the electromagnetic system comprising a field transmitter,
wherein providing the vision feature comprises providing a shadowing feature,
wherein the particular context of use comprises at least one of a medical context and a surgical context,
wherein providing the proprioception feature and providing the vision feature comprise configuring the proprioception feature and the vision feature, together, to optimize the 3D perception in relation to an interrogation volume by at least one of:

implementing focused visual targets by maintaining at least one of a focal plane and a focal point, using visual obscuration throughout the interrogation volume, and using a focused target in the depth dimension;

implementing serial focus adjustments by performing dynamic adjustment of a focal distance to create multiple focal points across a range of the interrogation volume; and implementing an immersive contextual volume of view by generating a volume of view in simultaneous focus, whereby continuous contextual information throughout the interrogation volume is provided, wherein providing the communication feature comprises providing at least one sensory input device and providing at least one sensory output device, and wherein providing the communication feature comprises providing the communication feature as operable by way of a set of executable instructions storable on a nontransitory memory device.

20. A method enhancing feedback during a medical procedure by way of a 3D navigation system, the method comprising:

providing the 3D navigation system, providing the 3D navigation system comprising:

providing an optical imaging system, providing the optical imaging system comprising:

providing an optical assembly comprising providing movable zoom optics and providing movable focus optics;

providing a zoom actuator for positioning the zoom optics; providing a focus actuator for positioning the focus optics;

providing a controller for controlling the zoom actuator and the focus actuator in response to received control input;

providing at least one detector for capturing an image of at least one of a target and an obstacle, providing the at least one detector comprising providing the at least one detector as operable with the optical assembly; and providing a proprioception feature operable with the optical imaging system for generating and enhancing a 3D perception, providing the proprioception feature comprising providing a communication feature configured to provide 3D information, providing the communication feature comprising providing a tracked tool and providing a capture feature, providing the capture feature comprising providing a 3D infrared (IR) optical tracking stereo camera, the 3D information comprising real-time depth information in relation to real-time planar information in relation to an interrogation volume, providing the capture feature comprising configuring the capture feature to acquire 3D image data by inwardly precessing in a spiral pattern and outwardly precessing in the spiral pattern within an interrogation volume, whereby acquired 3D image data is provided, and the providing capture feature comprising providing capture feature with a sensory device for translating the acquired 3D image data into a usable form, whereby translated acquired image data is provided;

providing a display device for presenting the 3D information, based on the translated data, the 3D information applicable to a particular context of use, providing the communication feature comprising providing at least one sensory input device and providing at least one sensory output device, and providing the communication feature comprises providing the communication feature as operable by way of a set of executable instructions storable on a nontransitory memory device, providing the zoom optics and providing the focus optics comprising respectively providing the zoom optics and providing the focus optics as independently movable by the controller by way of the zoom actuator and the focus actuator, respectively, and providing the optical imaging system comprising configuring the optical imaging system to operate at a minimum working distance from at least one of the target and the obstacle, the working distance defined between an aperture of the optical assembly and at least one of the target and the obstacle;

receiving at least one input signal by the at least one sensory input device; and providing at least one output signal by the at least one sensory output device, thereby enhancing feedback during the medical procedure.

* * * * *